US010427162B2

(12) United States Patent
Lei et al.

(10) Patent No.: US 10,427,162 B2
(45) Date of Patent: Oct. 1, 2019

(54) SYSTEMS AND METHODS FOR MOLECULAR DIAGNOSTICS

(71) Applicant: QuanDx Inc., San Jose, CA (US)

(72) Inventors: Xiaojun Lei, San Jose, CA (US); Yuan Yuan, San Jose, CA (US); Qian Xu, Rancho Cucamonga, CA (US); Paul Fleming, San Ramon, CA (US); Ronan Hayes, Monte Sereno, CA (US); Brian Lewis, Los Gatos, CA (US); Bruce Richardson, Los Gatos, CA (US)

(73) Assignee: QuanDx Inc., San Jose, CA (US)

( * ) Notice: Subject to any disclaimer, the term of this patent is extended or adjusted under 35 U.S.C. 154(b) by 43 days.

(21) Appl. No.: 15/385,873

(22) Filed: Dec. 21, 2016

(65) Prior Publication Data

US 2018/0169658 A1 Jun. 21, 2018

(51) Int. Cl.

| | |
|---|---|
| ***B01L 7/00*** | (2006.01) |
| ***B01L 3/00*** | (2006.01) |
| *C12Q 1/68* | (2018.01) |
| *B01L 3/02* | (2006.01) |

(52) U.S. Cl.

CPC ............... *B01L 7/52* (2013.01); *B01L 3/5085* (2013.01); *B01L 3/0275* (2013.01); *B01L 2200/0631* (2013.01); *B01L 2200/10* (2013.01); *B01L 2200/16* (2013.01); *B01L 2300/021* (2013.01); *B01L 2300/022* (2013.01); *B01L 2300/044* (2013.01)

(58) Field of Classification Search

CPC ............... B01L 3/502715; B01L 9/543; B01L 2300/021; B01L 2300/044; B01L 2300/0864; C12Q 1/686

USPC .......................................................... 422/500

See application file for complete search history.

(56) References Cited

U.S. PATENT DOCUMENTS

| | | | |
|---|---|---|---|
| 3,158,765 | A | 11/1964 | Polgreen |
| 3,662,279 | A | 5/1972 | Sandstrom et al. |
| 3,937,322 | A | 2/1976 | Cohen |
| 4,052,161 | A | 10/1977 | Atwood et al. |
| 4,101,070 | A | 7/1978 | Hoare et al. |
| 4,119,381 | A | 10/1978 | Muka et al. |
| 4,250,266 | A | 2/1981 | Wade |
| 4,401,189 | A | 8/1983 | Majewski |
| 4,486,539 | A | 12/1984 | Ranki et al. |
| 4,501,495 | A | 2/1985 | Faulkner et al. |
| 4,530,056 | A | 7/1985 | MacKinnon et al. |
| 4,593,238 | A | 6/1986 | Yamamoto |
| 4,593,239 | A | 6/1986 | Yamamoto |
| 4,673,657 | A | 6/1987 | Christian |
| 4,674,640 | A | 6/1987 | Asa et al. |
| 4,676,952 | A | 6/1987 | Edelmann et al. |
| 4,683,195 | A | 7/1987 | Mullis et al. |
| 4,683,202 | A | 7/1987 | Mullis |
| 4,751,177 | A | 6/1988 | Stabinsky |
| 4,780,817 | A | 10/1988 | Lofgren |

(Continued)

*Primary Examiner* — Rebecca M Fritchman

(74) *Attorney, Agent, or Firm* — Jun He Law Offices P.C.; James J. Zhu

(57) ABSTRACT

The present disclosure provides systems, devices and methods associates with processing and analyzing samples for molecular diagnostics. The system may process samples using assay cartridges including sample preparation modules and PCR modules. The system may include thermal cycler modules and optics modules to detect the specific nucleic acid sequences in the samples.

12 Claims, 24 Drawing Sheets

(56) References Cited

U.S. PATENT DOCUMENTS

| | | | |
|---|---|---|---|
| 4,800,159 | A | 1/1989 | Mullis et al. |
| 4,851,330 | A | 7/1989 | Kohne |
| 4,865,986 | A | 9/1989 | Coy et al. |
| 4,943,415 | A | 7/1990 | Przybylowicz et al. |
| 4,947,094 | A | 8/1990 | Dyer et al. |
| 4,950,613 | A | 8/1990 | Arnold, Jr. et al. |
| 5,004,582 | A | 4/1991 | Miyata et al. |
| 5,055,393 | A | 10/1991 | Kwoh et al. |
| 5,055,408 | A | 10/1991 | Higo et al. |
| 5,075,853 | A | 12/1991 | Luke, Jr. |
| 5,118,191 | A | 6/1992 | Hopkins |
| 5,147,529 | A | 9/1992 | Lee et al. |
| 5,154,888 | A | 10/1992 | Zander et al. |
| 5,158,895 | A | 10/1992 | Ashihara et al. |
| 5,168,766 | A | 12/1992 | Stoffel |
| 5,179,329 | A | 1/1993 | Nishikawa et al. |
| 5,185,439 | A | 2/1993 | Arnold, Jr. et al. |
| 5,186,827 | A | 2/1993 | Liberti et al. |
| 5,190,136 | A | 3/1993 | Grecksch et al. |
| 5,196,168 | A | 3/1993 | Muszak et al. |
| 5,205,393 | A | 4/1993 | Malow et al. |
| 5,229,297 | A | 7/1993 | Schnipelsky et al. |
| 5,234,665 | A | 8/1993 | Ohta et al. |
| 5,244,055 | A | 9/1993 | Shimizu |
| 5,283,174 | A | 2/1994 | Arnold, Jr. et al. |
| 5,283,739 | A | 2/1994 | Summerville et al. |
| 5,288,463 | A | 2/1994 | Chemelli |
| 5,330,916 | A | 7/1994 | Williams et al. |
| 5,350,564 | A | 9/1994 | Mazza et al. |
| 5,351,801 | A | 10/1994 | Markin et al. |
| 5,362,291 | A | 11/1994 | Williamson, IV |
| 5,366,896 | A | 11/1994 | Margrey et al. |
| 5,374,395 | A | 12/1994 | Robinson et al. |
| 5,375,898 | A | 12/1994 | Ohmori et al. |
| 5,380,487 | A | 1/1995 | Choperena et al. |
| 5,388,682 | A | 2/1995 | Dudley |
| 5,389,339 | A | 2/1995 | Petschek et al. |
| 5,397,709 | A | 3/1995 | Berndt |
| 5,399,491 | A | 3/1995 | Kacian et al. |
| 5,403,711 | A | 4/1995 | Walder et al. |
| 5,411,876 | A | 5/1995 | Bloch et al. |
| 5,415,839 | A | 5/1995 | Zaun et al. |
| 5,422,271 | A | 6/1995 | Chen et al. |
| 5,427,930 | A | 6/1995 | Birkenmeyer et al. |
| 5,437,990 | A | 8/1995 | Burg et al. |
| 5,443,791 | A | 8/1995 | Cathcart et al. |
| 5,447,687 | A | 9/1995 | Lewis et al. |
| 5,449,602 | A | 9/1995 | Royer et al. |
| 5,462,881 | A | 10/1995 | Perlman |
| 5,466,574 | A | 11/1995 | Liberti et al. |
| 5,480,784 | A | 1/1996 | Kacian et al. |
| 5,482,834 | A | 1/1996 | Gillespie |
| 5,504,345 | A | 4/1996 | Bartunek et al. |
| 5,514,550 | A | 5/1996 | Findlay et al. |
| 5,525,300 | A | 6/1996 | Danssaert et al. |
| 5,527,673 | A | 6/1996 | Reinhartz et al. |
| 5,536,649 | A | 7/1996 | Fraiser et al. |
| 5,538,849 | A | 7/1996 | Uematsu et al. |
| 5,554,516 | A | 9/1996 | Kacian et al. |
| 5,563,037 | A | 10/1996 | Sutherland et al. |
| 5,578,270 | A | 11/1996 | Reichler et al. |
| 5,582,796 | A | 12/1996 | Carey et al. |
| 5,585,242 | A | 12/1996 | Bouma et al. |
| 5,585,481 | A | 12/1996 | Arnold, Jr. et al. |
| 5,587,128 | A | 12/1996 | Wilding et al. |
| 5,589,333 | A | 12/1996 | Bagasra et al. |
| 5,602,042 | A | 2/1997 | Farber |
| 5,604,130 | A | 2/1997 | Warner et al. |
| 5,612,200 | A | 3/1997 | Dattagupta et al. |
| 5,612,525 | A | 3/1997 | Apter et al. |
| 5,616,301 | A | 4/1997 | Moser et al. |
| 5,623,415 | A | 4/1997 | O'Bryan et al. |
| 5,628,962 | A | 5/1997 | Kanbara et al. |
| 5,637,275 | A | 6/1997 | Carey et al. |
| 5,639,599 | A | 6/1997 | Ryder et al. |
| 5,639,604 | A | 6/1997 | Arnold, Jr. et al. |
| 5,641,658 | A | 6/1997 | Adams et al. |
| 5,648,727 | A | 7/1997 | Tyberg et al. |
| 5,652,489 | A | 7/1997 | Kawakami |
| 5,653,940 | A | 8/1997 | Carey et al. |
| 5,656,493 | A | 8/1997 | Mullis et al. |
| 5,665,554 | A | 9/1997 | Reeve et al. |
| 5,679,553 | A | 10/1997 | Van Gemen et al. |
| 5,686,272 | A | 11/1997 | Marshall et al. |
| 5,688,643 | A | 11/1997 | Oka et al. |
| 5,702,950 | A | 12/1997 | Tajima |
| 5,705,062 | A | 1/1998 | Knobel |
| 5,714,380 | A | 2/1998 | Neri et al. |
| 5,720,923 | A | 2/1998 | Haff et al. |
| 5,723,591 | A | 3/1998 | Livak et al. |
| 5,730,938 | A | 3/1998 | Carbonari et al. |
| 5,735,587 | A | 4/1998 | Malin et al. |
| 5,741,708 | A | 4/1998 | Carey et al. |
| 5,746,978 | A | 5/1998 | Bienhaus et al. |
| 5,750,338 | A | 5/1998 | Collins et al. |
| 5,773,268 | A | 6/1998 | Korenberg et al. |
| 5,779,981 | A | 7/1998 | Danssaert et al. |
| 5,786,182 | A | 7/1998 | Catanzariti et al. |
| 5,795,547 | A | 8/1998 | Moser et al. |
| 5,798,263 | A | 8/1998 | Wood et al. |
| 5,814,008 | A | 9/1998 | Chen et al. |
| 5,814,276 | A | 9/1998 | Riggs |
| 5,814,961 | A | 9/1998 | Imahashi |
| 5,827,653 | A | 10/1998 | Sammes et al. |
| 5,846,489 | A | 12/1998 | Bienhaus et al. |
| 5,846,491 | A | 12/1998 | Choperena et al. |
| 5,846,726 | A | 12/1998 | Nadeau et al. |
| 5,857,955 | A | 1/1999 | Phillips et al. |
| 5,866,336 | A | 2/1999 | Nazarenko et al. |
| 5,881,781 | A | 3/1999 | Bishop |
| 5,882,903 | A | 3/1999 | Andrevski et al. |
| 5,894,347 | A | 4/1999 | MacDonald |
| 5,895,631 | A | 4/1999 | Tajima |
| 5,897,783 | A | 4/1999 | Howe et al. |
| 5,914,230 | A | 6/1999 | Liu et al. |
| 5,919,622 | A | 7/1999 | Macho et al. |
| 5,922,591 | A | 7/1999 | Anderson et al. |
| 5,925,517 | A | 7/1999 | Tyagi et al. |
| 5,928,907 | A | 7/1999 | Woudenberg et al. |
| 5,948,673 | A | 9/1999 | Cottingham |
| 5,966,309 | A | 10/1999 | O'Bryan et al. |
| 5,972,693 | A | 10/1999 | Rothberg et al. |
| 5,994,056 | A | 11/1999 | Higuchi |
| 6,011,508 | A | 1/2000 | Perreault et al. |
| 6,033,574 | A | 3/2000 | Siddiqi |
| 6,033,880 | A | 3/2000 | Haff et al. |
| 6,043,880 | A | 3/2000 | Andrews et al. |
| 6,049,745 | A | 4/2000 | Douglas et al. |
| 6,056,106 | A | 5/2000 | van Dyke, Jr. et al. |
| 6,060,022 | A | 5/2000 | Pang et al. |
| 6,063,340 | A | 5/2000 | Lewis et al. |
| 6,068,978 | A | 5/2000 | Zaun et al. |
| 6,071,395 | A | 6/2000 | Lange |
| 6,096,561 | A | 8/2000 | Tayi |
| 6,100,079 | A | 8/2000 | Tajima |
| 6,110,676 | A | 8/2000 | Coull et al. |
| 6,110,678 | A | 8/2000 | Weisburg et al. |
| 6,117,398 | A | 9/2000 | Bienhaus et al. |
| 6,129,428 | A | 10/2000 | Helwig et al. |
| 6,150,097 | A | 11/2000 | Tyagi et al. |
| 6,165,778 | A | 12/2000 | Kedar |
| 6,171,780 | B1 | 1/2001 | Pham et al. |
| 6,197,572 | B1 | 3/2001 | Schneebeli |
| 6,212,448 | B1 | 4/2001 | Xydis |
| 6,277,332 | B1 | 8/2001 | Sucholeiki |
| 6,300,068 | B1 | 10/2001 | Burg et al. |
| 6,300,138 | B1 | 10/2001 | Gleason et al. |
| 6,306,658 | B1 | 10/2001 | Turner et al. |
| 6,333,008 | B1 | 12/2001 | Leistner et al. |
| 6,335,166 | B1 | 1/2002 | Ammann et al. |
| 6,353,774 | B1 | 3/2002 | Goldenberg et al. |
| 6,368,872 | B1 | 4/2002 | Juranas |
| 6,370,452 | B1 | 4/2002 | Pfister |
| 6,374,989 | B1 | 4/2002 | van Dyke, Jr. et al. |

(56) References Cited

U.S. PATENT DOCUMENTS

| | | | |
|---|---|---|---|
| 6,377,888 | B1 | 4/2002 | Olch |
| 6,413,780 | B1 | 7/2002 | Bach et al. |
| 6,429,016 | B1 | 8/2002 | McNeil |
| 6,436,349 | B1 | 8/2002 | Carey et al. |
| 6,444,171 | B1 | 9/2002 | Sakazume et al. |
| RE37,891 | E | 10/2002 | Collins et al. |
| 6,458,324 | B1 | 10/2002 | Schinzel |
| 6,520,313 | B1 | 2/2003 | Kaarakainen et al. |
| 6,548,026 | B1 | 4/2003 | Dales et al. |
| 6,558,947 | B1 | 5/2003 | Lund et al. |
| 6,586,234 | B1 | 7/2003 | Burg et al. |
| 6,586,255 | B1 | 7/2003 | Hubert et al. |
| 6,595,696 | B1 | 7/2003 | Zellak |
| 6,597,450 | B1 | 7/2003 | Andrews et al. |
| 6,599,476 | B1 | 7/2003 | Watson et al. |
| 6,605,213 | B1 | 8/2003 | Ammann et al. |
| 6,629,028 | B2 | 9/2003 | Paromtchik et al. |
| 6,633,785 | B1 | 10/2003 | Kasahara et al. |
| 6,692,708 | B2 | 2/2004 | Chandler, Jr. |
| 6,764,649 | B2 | 7/2004 | Ammann |
| 6,770,883 | B2 | 8/2004 | McNeal et al. |
| 6,818,183 | B2 | 11/2004 | Hajduk et al. |
| 6,890,742 | B2 | 5/2005 | Ammann et al. |
| 6,919,058 | B2 | 7/2005 | Andersson et al. |
| 6,919,175 | B1 | 7/2005 | Bienhaus et al. |
| 6,941,200 | B2 | 9/2005 | Sonoyama et al. |
| 6,993,176 | B2 | 1/2006 | Yamagishi et al. |
| 7,033,820 | B2 | 4/2006 | Ammann et al. |
| 7,045,358 | B2 | 5/2006 | Chandler, Jr. |
| 7,071,006 | B2 | 7/2006 | Tajima et al. |
| 7,078,698 | B2 | 7/2006 | Itoh |
| 7,118,892 | B2 | 10/2006 | Ammann et al. |
| 7,135,145 | B2 | 11/2006 | Ammann et al. |
| 7,174,836 | B2 | 2/2007 | Marino et al. |
| 7,267,795 | B2 | 9/2007 | Ammann et al. |
| 7,269,480 | B2 | 9/2007 | Hashimoto et al. |
| 7,273,749 | B1 | 9/2007 | Wittwer et al. |
| 7,288,229 | B2 | 10/2007 | Turner et al. |
| 7,362,258 | B2 | 4/2008 | Kawabe et al. |
| 7,419,830 | B2 | 9/2008 | Canos et al. |
| 7,463,948 | B2 | 12/2008 | Orita |
| 7,473,897 | B2 | 1/2009 | Braendle et al. |
| 7,482,143 | B2 | 1/2009 | Ammann et al. |
| 7,499,581 | B2 | 3/2009 | Tribble et al. |
| 7,524,652 | B2 | 4/2009 | Ammann et al. |
| 7,560,255 | B2 | 7/2009 | Ammann et al. |
| 7,560,256 | B2 | 7/2009 | Ammann et al. |
| 7,666,681 | B2 | 2/2010 | Ammann et al. |
| 7,688,448 | B2 | 3/2010 | Bamberg et al. |
| 7,771,659 | B2 | 8/2010 | Ziegler |
| 8,074,578 | B2 | 12/2011 | Thornton |
| 8,192,992 | B2 | 6/2012 | Ammann et al. |
| 8,600,168 | B2 | 12/2013 | Dube et al. |
| 8,962,308 | B2 | 2/2015 | Wilson et al. |
| 2002/0025064 | A1 | 2/2002 | Itoh |
| 2002/0028489 | A1 | 3/2002 | Ammann et al. |
| 2002/0031768 | A1 | 3/2002 | McMillan et al. |
| 2002/0077239 | A1 | 6/2002 | Evans, III |
| 2002/0086417 | A1 | 7/2002 | Chen |
| 2002/0098117 | A1 | 7/2002 | Ammann et al. |
| 2002/0123156 | A1 | 9/2002 | Tajima |
| 2002/0137194 | A1 | 9/2002 | Ammann et al. |
| 2002/0137197 | A1 | 9/2002 | Ammann |
| 2002/0147515 | A1 | 10/2002 | Fava |
| 2003/0026736 | A1 | 2/2003 | Hajduk et al. |
| 2003/0027206 | A1 | 2/2003 | Ammann |
| 2003/0054542 | A1 | 3/2003 | Burns |
| 2003/0129614 | A1 | 7/2003 | Parameswaran et al. |
| 2003/0190755 | A1 | 10/2003 | Turner et al. |
| 2003/0213313 | A1 | 11/2003 | Katagi |
| 2003/0221771 | A1 | 12/2003 | Chang et al. |
| 2003/0223916 | A1 | 12/2003 | Testrut et al. |
| 2004/0029260 | A1 | 2/2004 | Hansen et al. |
| 2004/0076983 | A1 | 4/2004 | Karlsen |
| 2004/0081586 | A1 | 4/2004 | Mauchan et al. |
| 2004/0087426 | A1 | 5/2004 | Lattanzi |
| 2004/0115796 | A1 | 6/2004 | Burns |
| 2004/0158355 | A1 | 8/2004 | Holmqvist |
| 2004/0184959 | A1 | 9/2004 | Itoh |
| 2004/0206419 | A1 | 10/2004 | Ganz |
| 2004/0213651 | A1 | 10/2004 | Malin |
| 2005/0047973 | A1 | 3/2005 | Schulz et al. |
| 2005/0123457 | A1 | 6/2005 | Tajima et al. |
| 2005/0130198 | A1 | 6/2005 | Ammann et al. |
| 2005/0158212 | A1 | 7/2005 | Yavilevich |
| 2005/0163354 | A1 | 7/2005 | Ziegler |
| 2005/0207937 | A1 | 9/2005 | Itoh |
| 2005/0220670 | A1 | 10/2005 | Palmieri |
| 2005/0233370 | A1 | 10/2005 | Ammann et al. |
| 2005/0239127 | A1 | 10/2005 | Ammann et al. |
| 2005/0266489 | A1 | 12/2005 | Ammann et al. |
| 2006/0003373 | A1 | 1/2006 | Ammann et al. |
| 2006/0014295 | A1 | 1/2006 | Ziegler |
| 2006/0020370 | A1 | 1/2006 | Abramson |
| 2006/0093517 | A1 | 5/2006 | Yokoyama |
| 2006/0148063 | A1 | 7/2006 | Fauzzi |
| 2006/0228268 | A1 | 10/2006 | Heimberg et al. |
| 2006/0275888 | A1 | 12/2006 | Hibino |
| 2007/0044676 | A1 | 3/2007 | Clark et al. |
| 2007/0059209 | A1 | 3/2007 | Pang et al. |
| 2007/0100498 | A1 | 5/2007 | Matsumoto |
| 2007/0110634 | A1 | 5/2007 | Heimberg et al. |
| 2007/0134131 | A1 | 6/2007 | Watson et al. |
| 2007/0179690 | A1 | 8/2007 | Stewart |
| 2007/0184548 | A1 | 8/2007 | Tan |
| 2007/0189925 | A1 | 8/2007 | Blecka et al. |
| 2007/0193859 | A1 | 8/2007 | Kyutoku et al. |
| 2007/0196237 | A1 | 8/2007 | Neuzil et al. |
| 2007/0208440 | A1 | 9/2007 | Bliss et al. |
| 2007/0225901 | A1 | 9/2007 | Yamaguchi |
| 2007/0225906 | A1 | 9/2007 | Ikeda |
| 2007/0292941 | A1 | 12/2007 | Handique et al. |
| 2008/0014181 | A1 | 1/2008 | Ariff |
| 2008/0015470 | A1 | 1/2008 | Sarstedt |
| 2008/0056958 | A1 | 3/2008 | Vijay et al. |
| 2008/0069730 | A1 | 3/2008 | Itoh |
| 2008/0138249 | A1 | 6/2008 | Itoh |
| 2008/0167817 | A1 | 7/2008 | Hessler et al. |
| 2008/0241837 | A1 | 10/2008 | Ammann et al. |
| 2008/0248586 | A1 | 10/2008 | Tajima |
| 2008/0255683 | A1 | 10/2008 | Takahashi et al. |
| 2008/0268528 | A1 | 10/2008 | Ammann et al. |
| 2008/0274511 | A1 | 11/2008 | Tan |
| 2008/0286151 | A1 | 11/2008 | Chang et al. |
| 2008/0297769 | A1 | 12/2008 | Bamberg |
| 2009/0029352 | A1 | 1/2009 | Ammann et al. |
| 2009/0029871 | A1 | 1/2009 | Ammann et al. |
| 2009/0029877 | A1 | 1/2009 | Ammann et al. |
| 2009/0030551 | A1 | 1/2009 | Hein |
| 2009/0035185 | A1 | 2/2009 | Tsujimura |
| 2009/0042281 | A1 | 2/2009 | Chang et al. |
| 2009/0047179 | A1 | 2/2009 | Ping |
| 2009/0117004 | A1 | 5/2009 | Fritchie et al. |
| 2009/0117620 | A1 | 5/2009 | Fritchie et al. |
| 2009/0130745 | A1 | 5/2009 | Williams et al. |
| 2009/0283512 | A1 | 11/2009 | Huhn et al. |
| 2009/0318276 | A1 | 12/2009 | Miller |
| 2009/0324032 | A1 | 12/2009 | Chen |
| 2010/0018330 | A1 | 1/2010 | Marty |
| 2010/0115887 | A1 | 5/2010 | Schroeder et al. |
| 2010/0129789 | A1 | 5/2010 | Self |
| 2010/0141756 | A1 | 6/2010 | Grote |
| 2010/0261595 | A1 | 10/2010 | Schaefer |
| 2010/0291619 | A1 | 11/2010 | Robinson et al. |
| 2011/0065193 | A1 | 3/2011 | Kitagawa |
| 2011/0226584 | A1 | 9/2011 | Ek |
| 2012/0129673 | A1 | 5/2012 | Fukugaki et al. |
| 2012/0258516 | A1* | 10/2012 | Schultz ................. B01F 3/0807 435/194 |
| 2014/0038192 | A1 | 2/2014 | Buse et al. |

* cited by examiner

SYSTEMS AND METHODS FOR MOLECULAR DIAGNOSTICS

FIELD OF THE INVENTION

The present invention generally relates to systems and methods for molecular diagnostics.

BACKGROUND OF THE INVENTION

Many nucleic acid sequences have been used to diagnose and monitor disease, detect risk and decide which therapies will work best for individual patient. For example, the presence of nucleic acid sequences associated with infectious organisms may indicate an infection by the organism. The presence of an altered nucleic acid sequence in a patient sample may indicate activation or inactivation of a pathway related to a disease or disorders.

Detection of clinically related nucleic acid sequences in a sample generally involves isolating nucleic acid from the sample and amplification of specific nucleic acid sequences followed by detection of the amplified products. However, complexities of the multi-step process of isolating nucleic acid limit the processing flexibility and reduce the repeatability. For example, DNA and RNA have different chemical properties and stability, whose preparation requires different processing conditions. Further, samples from different source organism may require different steps to isolate nucleic acids. For example, isolating DNA from bacteria may use harsher conditions (e.g., higher temperature, higher concentration of detergent, etc.) than releasing DNA from relatively labile mammalian cells. Therefore, there is a need for an analytical system providing flexible and adjustable operating capabilities to meet the diverse demands of clinical diagnostics. Moreover, although amplification increases the sensitivity of the detection assay by providing sufficient copies of the specific nucleic acid sequences, it may risk erroneous results born of contamination. Therefore, there is also a need for an analytical system requiring minimal user participation to reduce contamination.

SUMMARY OF THE INVENTION

Embodiments of the present invention are directed to systems, devices and methods associated with processing and analyzing samples for molecular diagnostics. Embodiments of the invention include an automated, random access system for determining specific nucleic acid sequences in the sample.

In an aspect, the present invention provides an assay cartridge for a molecular diagnostic device. In one embodiment, the cartridge comprising a sample preparation module and a PCR module. In certain embodiments, the sample preparation module and the PCR module is detachably coupled.

In one embodiment, the sample preparation module and the PCR module is detachably coupled through a snap.

In one embodiment, the sample preparation module comprises a sample loading well comprising an inlet opening covered by a removable cap and an outlet covered by an outlet septum.

In one embodiment, the assay cartridge further comprises a marking element. In one embodiment, the marking element is selected from the groups consisting of a barcode, a dot code, a radio frequency identification tag (RFID) or a direct reading electronic memory.

In another aspect, the present disclosure provides a sample preparation module for an assay cartridge used in a molecular diagnostics device, said sample preparation module comprising an elongated body formed to comprise a sample loading well, wherein the sample loading well comprises an inlet opening covered by a removable cap, and an outlet covered by an outlet septum.

In one embodiment, the sample preparation module further comprises a formalin-fixed paraffin-embedded (FFPE) capture insert, wherein the removable cap comprises a plunger.

In one embodiment, the sample loading well includes a sample collecting channel having the outlet at the top end and a fluid collecting area at the bottom end.

In one embodiment, the sample loading well has a deepest portion at the fluid collecting area.

In one embodiment, the elongated body further comprises a purification well. In one embodiment, the purification well contains magnetic microparticles capable of binding to nucleic acid.

In one embodiment, the elongated body further comprises one or more reagent compartments.

In one embodiment, the elongated body further comprises a pipette tip holder.

In one embodiment, the pipette tip holder is preloaded with a pipette tip.

In yet another aspect, the present disclosure provides a PCR module for an assay cartridge used in a molecular diagnostics device. In one embodiment, the PCR module comprising an elongated body formed to comprise a push well; and at least one reaction well connected to the push well through a microfluidic channel.

In one embodiment, the push well is pre-loaded with a solution mixture including reagents for PCR reaction.

In one embodiment, the PCR module further comprises a barrier film covering the upper ends of the reaction well formed.

In one embodiment, the elongated body further comprises a plurality of reagent wells.

In one embodiment, the elongated body further comprises a pipette tip holder. In one embodiment, the pipette tip holder is preloaded with a pipette tip.

In another aspect, the present disclosure provides a cartridge carriage that can load the assay cartridge as disclosed above into a device for determining specific nucleic acid sequences in samples. In one embodiment, the cartridge carriage comprises a cavity configured to hold the assay cartridge. In one embodiment, the cartridge carriage comprises at least one sample vial holder. In one embodiment, the PCR wells of the assay cartridge are not loaded into the cavity when the assay cartridge is loaded into the carriage.

In one embodiment, the cartridge carriage comprises structure that secures the assay cartridge into appropriate position in the cavity. In one embodiment, the cartridge carriage comprises a groove located at the distal end of the cavity that fits a groove runner at the bottom of the assay cartridge. In one embodiment, the cartridge carriage comprises an opening at the bottom wall that allows the device to interact with the compartments of the assay cartridge thought its sides and edges. In one embodiment, the cartridge carrier includes a proximal fix tab and a distal fix tab that secures the cartridge carrier in appropriate location in the device.

In another aspect, the present disclosure provides a dispense system including a XYZ gantry with a pipettor for transferring a reagent between compartments in the assay cartridge as disclosed above. In one embodiment, the pipettor comprises a pipettor carriage that supports a pipettor head. In one embodiment, the pipettor contains a lift that can raise and lower the pipettor head.

In another aspect, the present disclosure provides a thermal cycler module configured to amplify a specific nucleic acid sequence in the PCR well of the assay cartridge disclosed above. In one embodiment, the thermal cycler comprises a thermal block and a receptacle for forming contact surface with a PCR well. In one embodiment, the receptacle comprises an optical aperture configured to permit optical communication through optical fibers to the interior of the receptacle. In one embodiment, the thermal cycler module further comprises a plurality of heat transfer fins.

In another aspect, the present disclosure provides an optic module for exciting dyes in and detecting fluorescence from the PCR wells in the assay cartridge disclosed above. In one embodiment, the optical module comprises a rotary plate that includes a plurality of filters each for a different wavelength, wherein the rotary plate is stacked on an optical fiber plate. In one embodiment, the filters are arranged on a circle from the center of the rotary plate and the terminus of the optical fibers are arranged on the optical fiber plate on a circle matching the one in the rotary plate so that when the rotary plate is rotated the filters can align with the optical fiber termini.

In another aspect, the present disclosure provides a system for processing a sample, the system comprising: at least one assay cartridge comprising at least a first compartment and a second compartment, wherein the first compartment contains liquid; a pipettor configured to transfer the liquid from the first compartment to the second compartment; and a controller configured to direct the pipettor to transfer the liquid from the first compartment to the second compartment; wherein the assay cartridge contains all the reagents needed for processing the sample.

In one embodiment, the assay cartridge comprises a reaction vessel for containing a nucleic acid purified from the sample.

In one embodiment, the system further comprises a thermal cycler module configured to amplify a nucleic acid sequence in the sample.

In one embodiment, the system further comprising an optic module configured to detect the presence of a nucleic acid sequence in the sample.

These and other features, aspects, and advantages of the present invention will become better understood with regard to the following description, appended claims and accompanying drawings.

DETAILED DESCRIPTION OF THE INVENTION

Figure 1A:
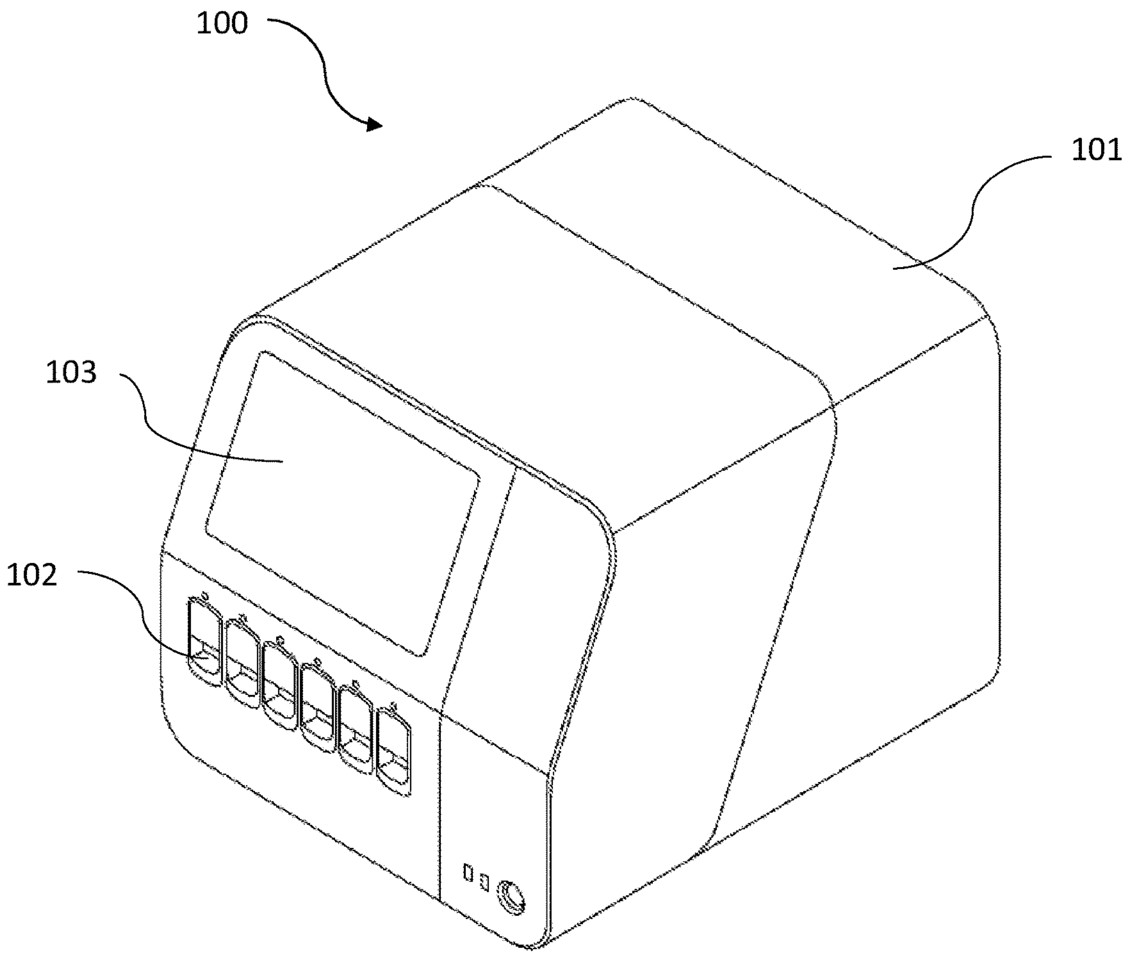
FIG. 1A shows a top perspective view of a device according to an embodiment of the invention.

In the Summary of the Invention above and in the Detailed Description of the Invention, and the claims below, and in the accompanying drawings, reference is made to particular features (including method steps) of the invention. It is to be understood that the disclosure of the invention in this specification includes all possible combinations of such particular features. For example, where a particular feature is disclosed in the context of a particular aspect or embodiment of the invention, or particular claim, that feature can also be used, to the extent possible, in combination with and/or in the context of other particular aspects and embodiments of the invention, and in the invention generally.

The term "comprises" and grammatical equivalents thereof are used herein to mean that other components, ingredients, steps, etc. are optionally present. For example, an article "comprising" (or "which comprises") components A, B, and C can consist of (i.e., contain only) components A, B, and C, or can contain not only components A, B, and C but also one or more other components.

Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

Where a range of value is provided, it is understood that each intervening value, to the tenth of the unit of the lower limit unless the context clearly dictate otherwise, between the upper and lower limit of that range and any other stated or intervening value in that stated range, is encompassed within the disclosure, subject to any specifically excluded limit in the stated range. Where the stated range includes one or both of the limits, ranges excluding either or both of those included limits are also included in the disclosure.

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, the embodiments described herein can be practiced without there specific details. In other instances, methods, procedures and components have not been described in detail so as not to obscure the related relevant function being described. Also, the description is not to be considered as limiting the scope of the implementations described herein. It will be understood that descriptions and characterizations of the embodiments set forth in this disclosure are not to be considered as mutually exclusive, unless otherwise noted.

The following definitions are used in the disclosure:

The term "at least" followed by a number is used herein to denote the start of a range beginning with that number (which may be a range having an upper limit or no upper limit, depending on the variable being defined). For example, "at least 1" means 1 or more than 1. The term "at most" followed by a number is used herein to denote the end of a range ending with that number (which may be a range having 1 or 0 as its lower limit, or a range having no lower limit, depending upon the variable being defined). For example, "at most 4" means 4 or less than 4, and "at most 40%" means 40% or less than 40%. When, in this specification, a range is given as "(a first number) to (a second number)" or "(a first number)-(a second number)," this means a range whose lower limit is the first number and whose upper limit is the second number. For example, 25 to 100 mm means a range whose lower limit is 25 mm, and whose upper limit is 100 mm.

PCR or "Polymerase Chain Reaction" refers to a method used to amplify DNA through repeated cycles of enzymatic replication followed by denaturation of the DNA duplex and formation of new DNA duplexes. Denaturation and renaturation of the DNA duplex may be performed by altering the temperature of the DNA amplification reaction mixture. Reverse-transcriptase PCR (RT-PCR) refers to a PCR process including a step to transcribing RNA (e.g., mRNA) into cDNA which is then amplified. Real time PCR refers to a PCR process in which a signal that is related to the amount of amplified DNA in the reaction is monitored during the amplification process. This signal is often fluorescence. However, other detection methods are possible. In an exemplary embodiment, a PCR subsystem takes a prepared and sealed reaction vessel and performs a complete realtime polymerase chain reaction analysis, thermal cycling the sample multiple times and reporting the intensity of emitted fluorescent light at each cycle.

Overall System Layout

In one aspect, the present disclosure provides a fully automated, random access system for determining specific nucleic acid sequences in samples. The system can combine two general functions: sample preparation in the form of isolating nucleic acids from a sample, and detection of specific sequences within the isolated nucleic acids. Toward this end, the system includes an assay cartridge that has at least two distinct functional modules: one for process samples to isolate nucleic acids and a second for nucleic acid amplification and detection. The system includes instrumentation that works on the assay cartridge to carry out the functions. In some embodiments, the instrumentation is contained in a single, enclosed device. The system also includes consumables incorporating necessary reagents for performance of a variety of assays and transfer devices (e.g., pipette tips). In certain embodiments, all consumables are contained in an assay cartridge so that there is no need to store any consumables in the device. The system may also include holders for samples, connections for power and information. These are integrated in a single unit to provide a system that performs major functions of sample handling, nucleic acid isolation, amplification and detection, and supporting functions such as supply and consumable management, information management and maintenance. In some embodiments, the system includes multiple assay cartridges, each of which can be processed independently and simultaneously, i.e., in a random access fashion.

Combining these functions into a single, highly automated, self-contained system provides seamless integration of molecular diagnostics into the workflow of the clinical laboratory. A further benefit is to perform all steps of nucleic acid determination to produce clinically acceptable results without the need for user intervention. The system allows users to load samples as they are available, and to perform determination on these samples based on the needs of the patients and physicians, without constraints on sample or analyte order being imposed by the system.

FIG. 1A shows a system for molecular diagnostics according to one embodiment of the invention. Referring to FIG. 1A, the system includes a device 100 having a generally rectangular housing 101 with sides defining the front, back, left and right sides, top and bottom as illustrated. The device also has an assay cartridge loading area 102 and a control panel 103. The housing can be made of any suitable material known in the art, such as metal, alloy or plastic. The control panel can include a touch screen through which user can enter a variety of functions, such as selecting nucleic acid purification protocols and amplification programs. The touch screen can also display the status and results of the assays.

Figure 1B:
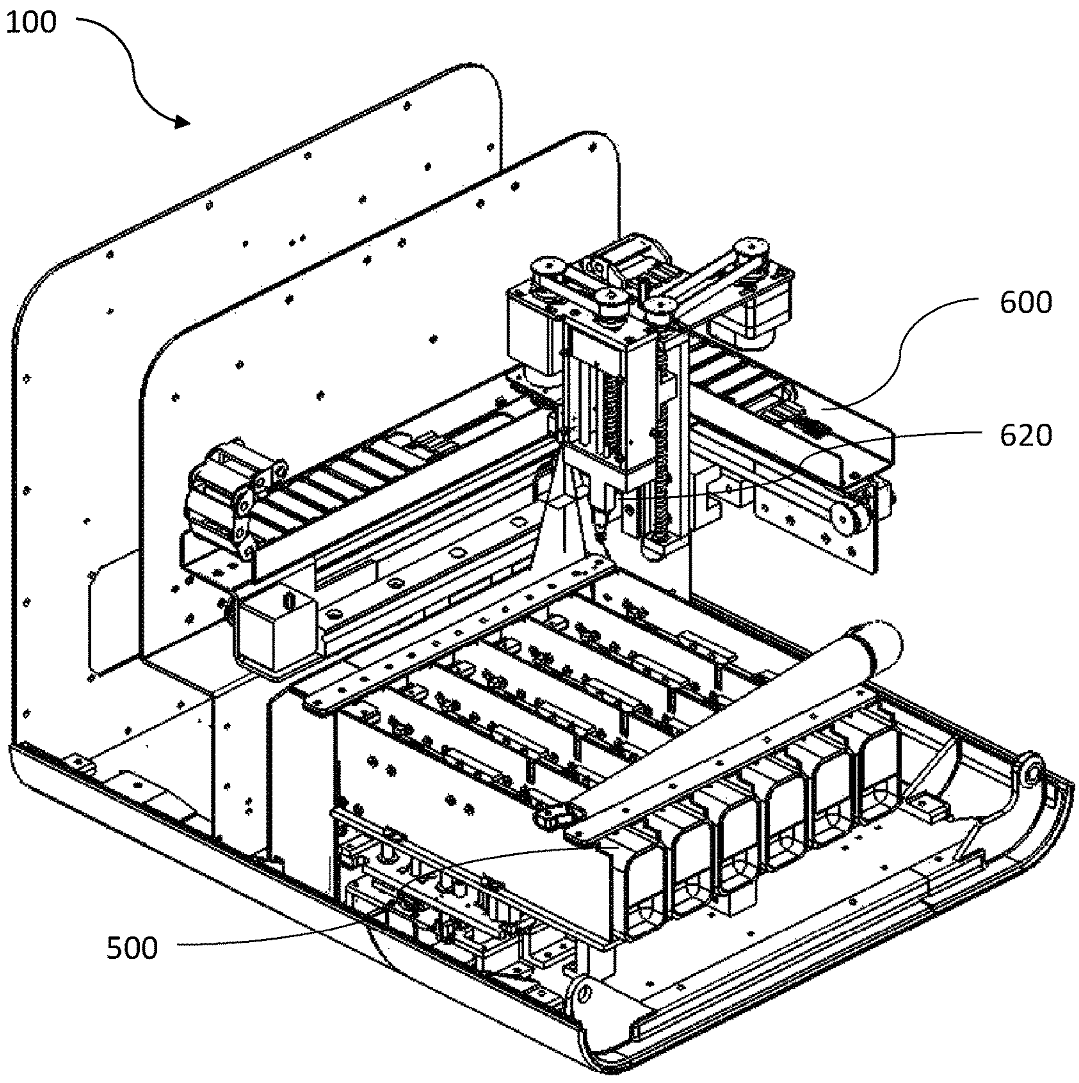
FIG. 1B shows a top perspective view of the layout of the components of the device.

FIG. 1B shows a top perspective view of the embodiment of FIG. 1A from above, with some components removed to clarify the basic structural and functional modules. Referring to FIG. 1B, the system includes a device 100 containing a cartridge loading unit 500 for receiving at least one assay cartridge comprising at least a first compartment and a second compartment (assay cartridge is not loaded as shown in FIG. 1B). In use, the assay cartridge is loaded into the device 100 through a cartridge carriage. The device 100 includes a dispense system 600 having at least one pipettor 620, which may transfer a reagent from the first compartment to the second compartment. The device 100 also includes a thermal cycler module for amplification, and an optical module for detecting products from the amplification.

Figure 1C:
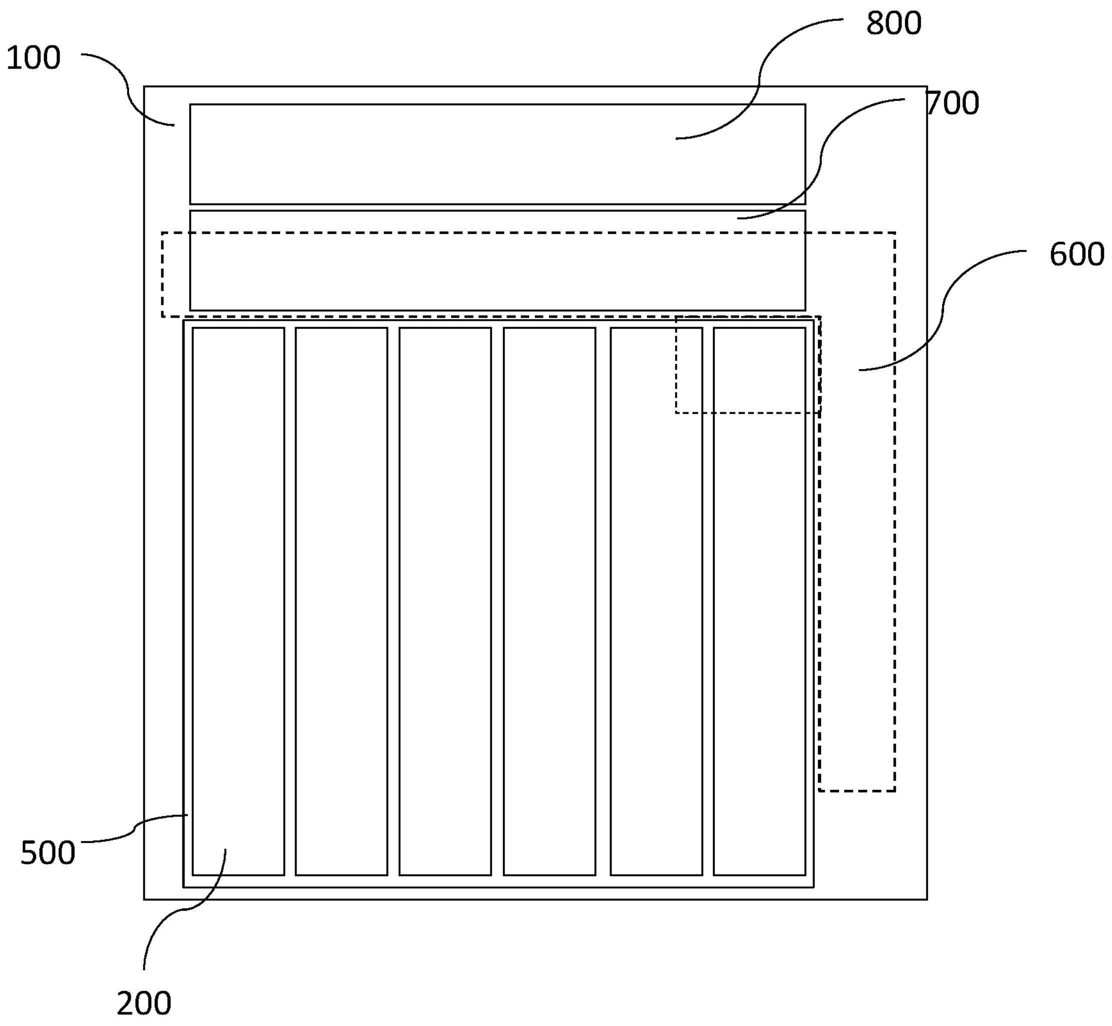
FIG. 1C shows a top plan view of the device.

FIG. 1C shows a top plan view of the layout of the embodiment of FIG. 1A from above. Referring to FIG. 1C, the system includes a device 100 having a cartridge loading unit 500 where a plurality of assay cartridges 200 are loaded.

Each assay cartridge 200 comprises at least a first compartment and a second compartment. In use, the assay cartridge 200 is loaded with a sample to be assayed. The assay cartridge 200 contains all consumables that are needed for the assay so that there is no need to store any consumables in the device 100. The system also includes a dispense system 600 having at least one pipettor, which may perform a variety of functions, such as transferring a reagent from the first compartment to the second compartment. The system further includes a thermal cycler module 700 that may assist the amplification of nucleic acid sequences in the sample loaded in the assay cartridge 200. The system also includes an optic module 800 responsible for exciting the dyes in the assay and detecting the fluorescence emitted at each PCR cycle.

In this embodiment, a method for using the system may comprise loading a plurality of assay cartridges into the cartridge loading unit, each assay cartridge loaded with a sample to be assayed, isolating nucleic acid from the sample by transferring and mixing the reagents stored in the assay cartridge using a dispense system having a pipettor, amplifying a specific nucleic acid sequence in the sample using a thermal cycler module, and detecting the presence of the nucleic acid sequence using an optic module.

This embodiment can provide flexibility in processing a plurality of samples. The system, in executing a first protocol, can process a first sample loaded in a first assay cartridge. Meanwhile, the system, in executing a second protocol, can also processing a second sample loaded in a second assay cartridge. The first and second protocols and their sequences of operations may differ in any suitable manner. For example, the first protocol can be directed to isolate DNA and the second protocol can be directed to isolate RNA. Likewise, the first and second protocols may include common processing steps, but may differ according to duration processing or the parameters used for processing. For instance, in some embodiments, two different protocols may have similar processing steps, but the processing steps may differ because they are performed at different temperatures and/or for different periods of time. In another example, two protocols may have similar steps, but they may be performed in different orders. For example, a first protocol may include steps A, B, and C performed in that order. A second protocol may include steps B, A, and C performed in that order. In yet another example, different protocols may include different sets of steps. For example, a first protocol may comprise steps A, B, C, and D, while a second protocol may comprise steps B, D, E, F, and G.

Further, the plurality of samples can be processed in any order. In some embodiments, a plurality of assay cartridges can be loaded into the device to start processing at about the same time. Alternatively, the system can execute a first protocol to process a first sample. During the processing of the first sample and without stopping the first protocol, the system can receive a second assay cartridge loaded with a second sample and start to execute a second protocol to process the second sample.

Assay Cartridge

In anther aspect, the present disclosure provides an assay cartridge used in a molecular diagnostic device. The assay cartridge can be one-time use consumables, or may be reusable. In certain embodiments, the assay cartridge comprises a sample preparation module and a PCR module. The sample preparation module is for purifying nucleic acids (e.g., genomic DNA, total RNA, etc.) from a sample (e.g., FFPE specimen, blood or saliva, etc.). The PCR module is for amplifying a target region in the purified nucleic acids. In certain embodiments, the sample preparation module and the PCR module are formed in one body. In some embodiments, the sample preparation module and the PCR module are separated pieces that can be assembled upon use in the device. This design allows users to assemble the assay cartridge in their own desired configuration to combine a sample preparation module with different PCR modules to perform different assays (e.g., genomic DNA amplification or reverse transcriptase PCR), or vice versa, and to detect different target genes. Alternatively, the assay cartridge can be made as one piece that is functionally divided into a sample preparation module and a PCR module.

Figure 2A:
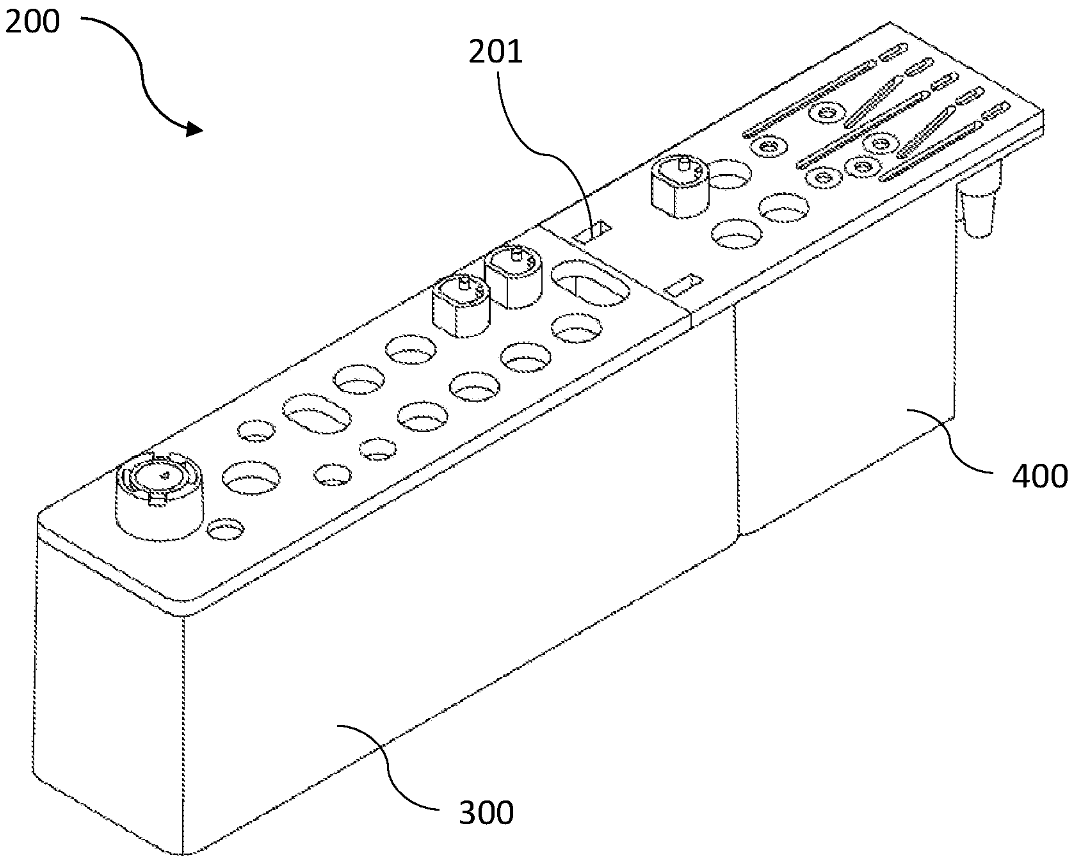
FIG. 2A shows a top perspective view of an assay cartridge according to one embodiment of the invention.
Figure 2B:
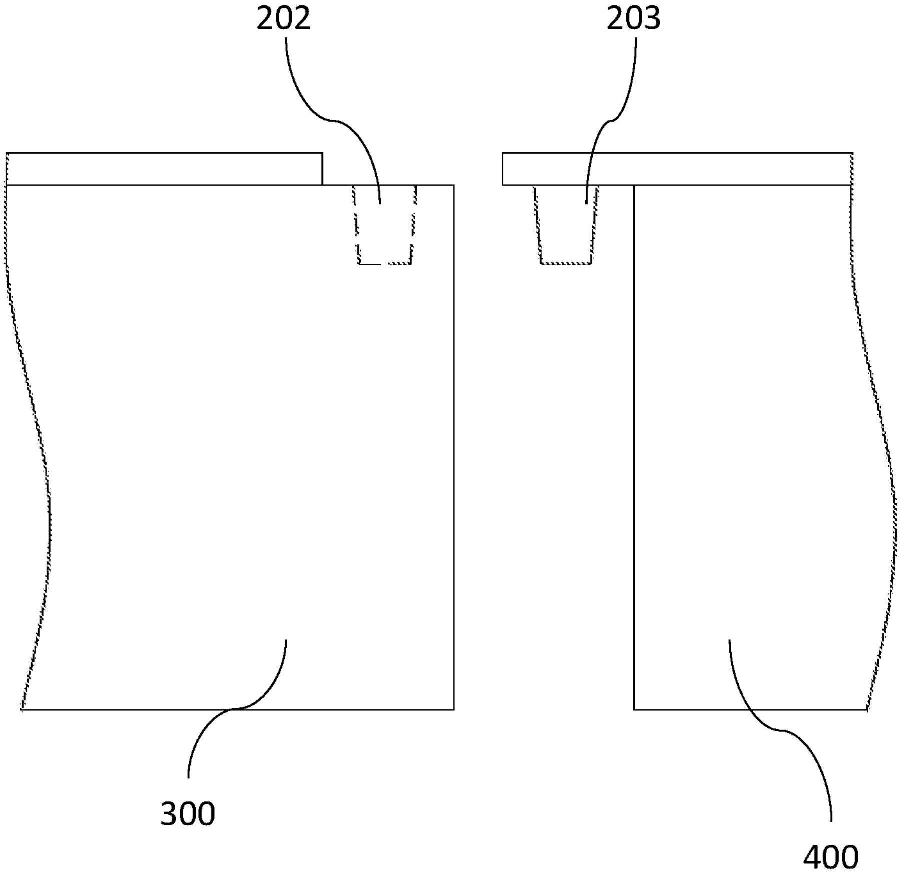
FIG. 2B shows a cross sectional view of a first half fastener located on the sample preparation module and a second half fastener located on the PCR module according to one embodiment of the invention.

FIGS. 2A-2B show one embodiment of an assay cartridge 200. The assay cartridge 200 comprises a sample preparation module 300 and a PCR module 400. The sample preparation module 300 and the PCR module 400 can be engaged through a snap structure 201. The snap structure 201 comprises a first half fastener 202 located on the sample preparation module 300 and a second half fastener 203 located on the PCR module 400. The sample preparation module 300 and the PCR module 400 can be engaged by pressing the first half fastener 202 and the second half fastener 203 together.

A. Sample Preparation Module

In one embodiment, the sample preparation module comprises an elongated body comprising a proximal end and a distal end, and a plurality of compartments arranged between the proximal end and the distal end, wherein at least one of the compartments is a sample loading well and at least one of the compartments is a purification well. The sample loading well is where a sample is loaded for procession before nucleic acids are extracted from the sample. The processed sample is transferred to the purification well to extract nucleic acids.

At least one of the compartments is a reagent storage well for storing reagents for nucleic acid (e.g., DNA or RNA) extraction from a sample. In one embodiment, the various compartments in the sample preparation module include all reagents needed for extracting nucleic acid from a sample. The reagents can include cell lysis solution, wash buffer and elution buffer.

The sample preparation module can include a pipette tip holder preloaded with a pipette tip (e.g., a microtip or a millitip) for transferring the fluids between the various compartments in the sample preparation module and/or between the sample preparation module and the PCR module.

Figure 3A:
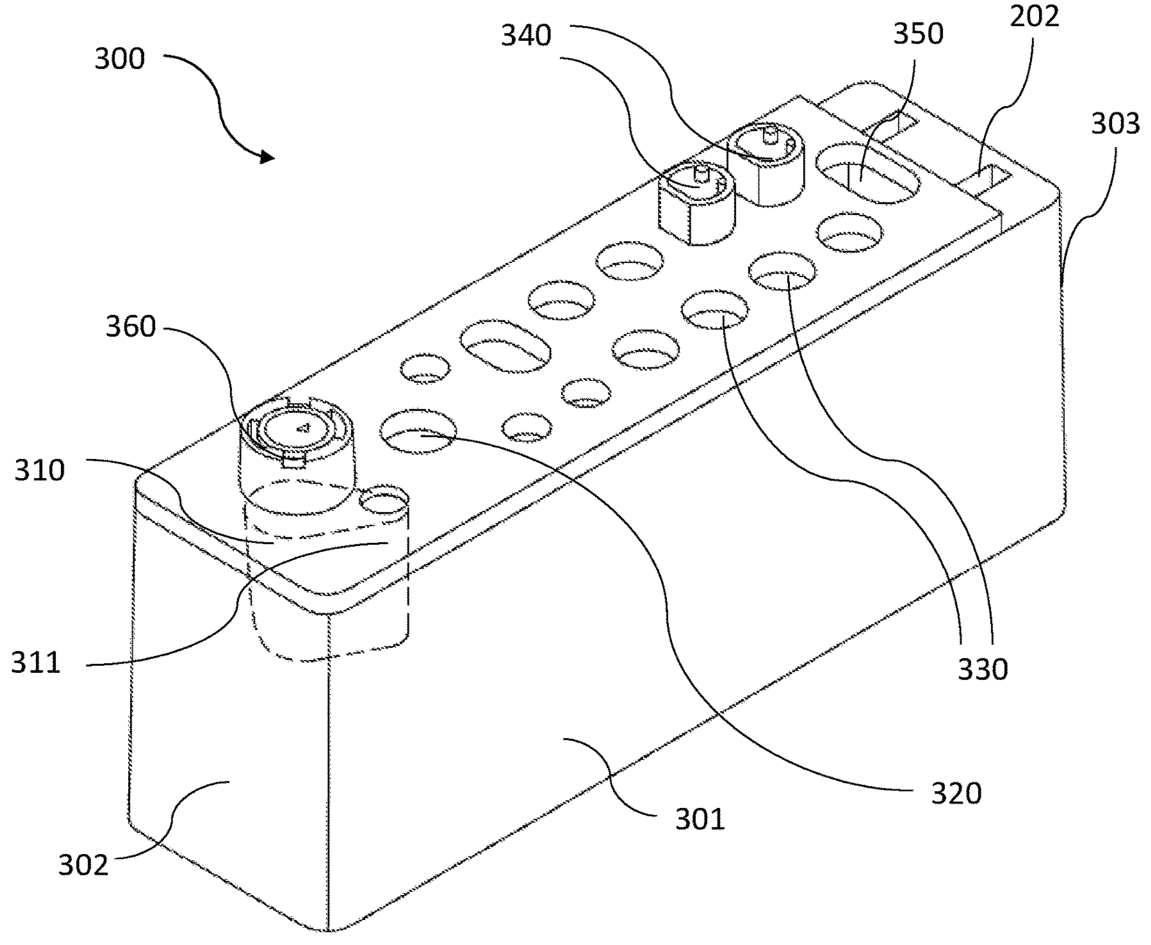
FIG. 3A shows a top perspective view of a sample preparation module of an assay cartridge according to one embodiment of the invention.

FIG. 3A shows one embodiment of a sample preparation module 300. The sample preparation module 300 comprises an elongated body 301 formed to include multiple compartments, which may hold fluids (e.g., reagents) and devices (e.g., pipette tips) needed to process various samples. Examples of compartments may include one or more sample loading wells 310, one or more purification wells 320, one or more reagent storage wells 330, one or more pipette tip holders 340, and one or more waste disposal wells 350. In certain embodiments, the sample preparation module 300 can be in the form a monolithic body, and may be formed of plastic (or any other suitable material). In certain embodiments, the sample preparation module 300 is made by a plastic injection molding process. Alternatively, the sample preparation module 300 is made by assembling individual components into a rigid framework. In one embodiment, several pieces of the sample preparation module 300, including a base formed to have the compartments and wells, and a cover plate having holes corresponding to each compartments and wells are made by a plastic injection molding process. To make the sample preparation module, the base and the cover plate are assembled to sandwich a barrier film (as described in detail infra).

The sample preparation module 300 can have a proximal end 302 and a distal end 303 at opposite ends of the elongated body 301. The orientation of the compartments defines the top and bottom portion of the sample preparation module 300. In certain embodiments, compartments can be open at the top and closed on the bottom and sides.

The sample preparation module 300 may also include a cap 360 that covers the opening of the sample loading well 310, optionally an FFPE insert for holding FFPE samples (see FIGS. 3B and 4B), a cover (e.g., a barrier film) that is disposed around various compartments, features to facilitate handling (e.g., a half fastener 202), selected reagents and labeling.

As shown in FIG. 3A, compartments within an sample preparation module 300 can be arranged in a generally linear layout, with the sample loading well 310 located near the proximal end 302, followed by the purification well 320, reagent storage wells 330, pipette tip holders 340, and waste disposal well 350 at the distal end 303. This layout allows simple motion of the dispense system (described in detail infra) to transfer the fluids among various compartments. Alternatively, the sample preparation module 300 can take different shape and arrangement of the compartments (e.g., an arc, a single-row linear, or a circle), depending on the overall system design, such as on the number and sequence of operative locations that need access to the individual compartments within a sample preparation module.

In some embodiments, the top ends of various compartments of a sample preparation module form openings that align at a common height. In some embodiments, compartment bottom ends generally do not align because various compartments differ in depth and shapes.

Compartments of the sample preparation module can perform a variety of functions. For example, the purification well 320 can provide a site for nucleic acid extraction. In addition, some compartments may perform more than one function. For example, reagent storage wells 330 initially contain reagents used in extracting nucleic acids may later hold wastes produced during purification process. And pipette tip holders 340 may later hold discarded pipette tips.

In some embodiments, various compartments lack common walls to prevent the creeping of liquids between compartments. This has the benefit of reducing the possibility of contamination between compartments. In some embodiments, the external profile of each compartment closely tracks the cavity internal profile, i.e., the walls of the compartment can be of relatively constant thickness and can be thin compared to the size of the compartment. One of the benefits of such design is to reduce the amount of material used and hence reduces the manufacturing cost of the module.

Figure 3B:
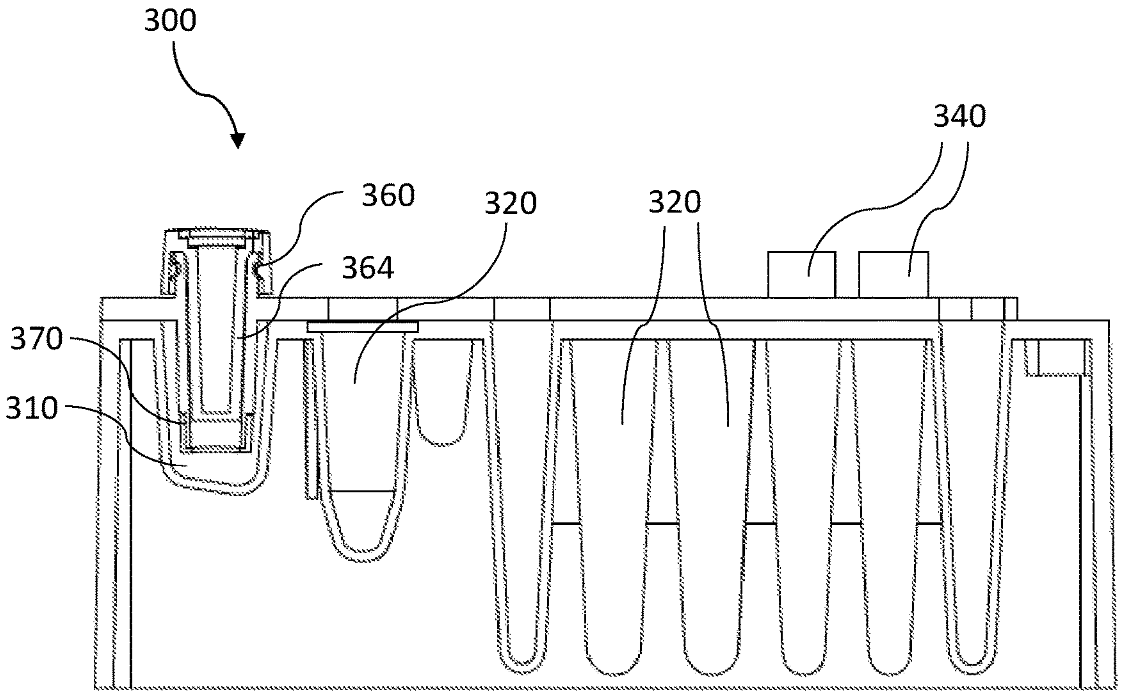
FIG. 3B shows a side, cross-sectional view of a sample preparation module.

FIG. 3B shows a side cross-section view of a sample preparation module 300. Referring to FIG. 3B, the sample preparation module 300 contains at least one sample loading well 310 where a sample for diagnostic analysis is loaded and processed. The sample loading well 310 is covered by a removable cap 360. The sample loading well 310 has a faceted shape designed to contain a relatively large reaction volume, to permit effective mixing of its contents, to permit aspiration with minimal dead volume. The sample loading well 310 can have a capacity of about 1000 microliters. In certain embodiments, the sample preparation module 300 includes a formalin-fixed paraffin-embedded (FFPE) sample insert 370 disposed in the sample loading well 310. The FFPE insert 370 can be used to hold FFPE sample when the sample is processed in the sample loading well 310. In such embodiment, the removable cap 360 includes a plunger 364 to push FFPE samples to the bottom of the FFPE insert 370.

Figure 4A:
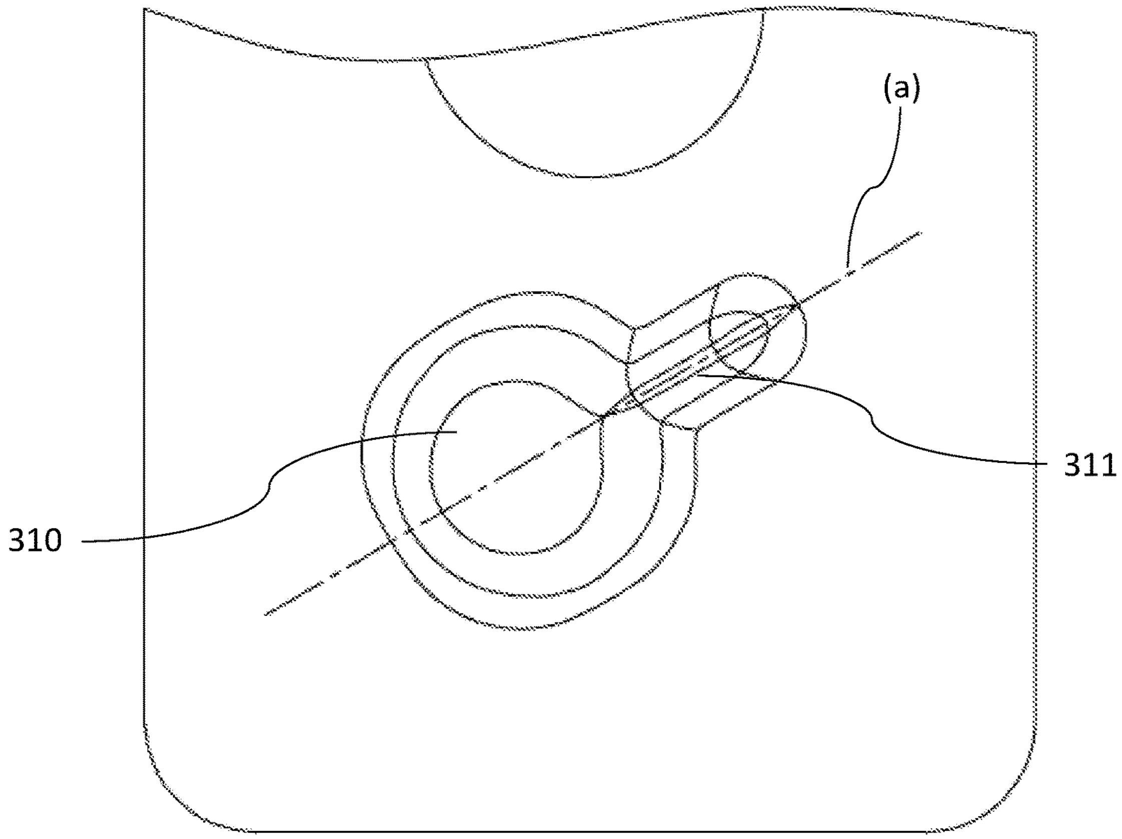
FIG. 4A shows a top view of a sample loading well according to one embodiment of the invention.

FIG. 4A shows a top view and a perspective view of a sample loading well according to an embodiment of the invention. As shown in FIG. 4A, the sample loading well 310 can have a generally rhombus cross-section in the horizontal plane with one diagonal axis of the rhombus aligned with the long axis of the sample preparation module. The sample loading well 310 can have an essentially vertical collecting channel 311 configured to allow a pipette tip to be inserted to the bottom of the sample loading well 310. The collecting channel 311 is arranged off-center and partially formed by the wall of the sample loading well 310. The structure of the collecting channel 311 is also illustrated in FIG. 4C, which is a cross-sectional view of the sample loading well through the plane (a).

Figure 4B:
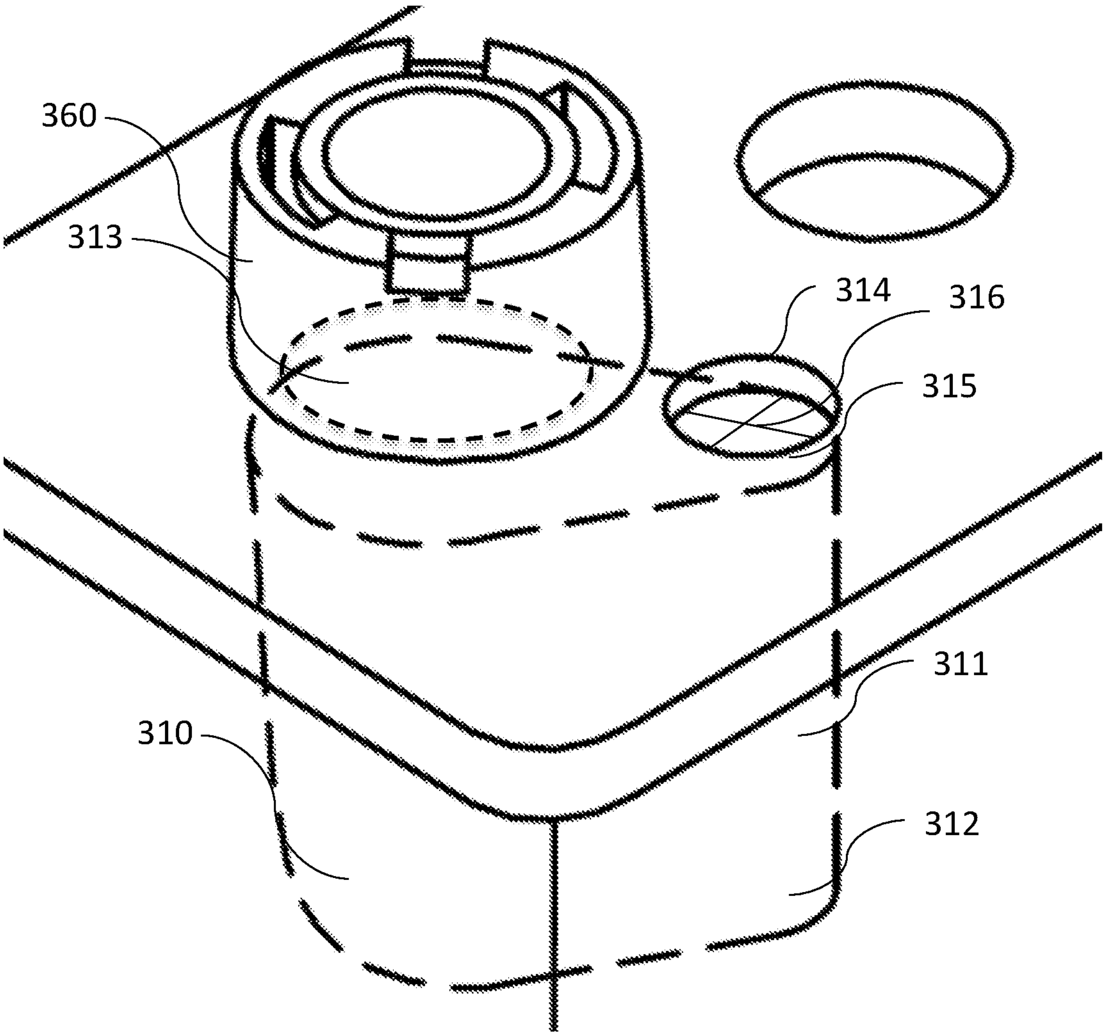
FIG. 4B shows a top perspective view of a sample loading well according to one embodiment of the invention.

FIG. 4B shows a perspective view of the sample loading well of FIG. 4A as shown above. Referring to FIG. 4B, the sample loading well 310 has an inlet opening 313 and an outlet 314. The inlet opening 313 can be covered by the removable cap 360. The bottom of the sample loading well 310 is configured to form a fluid collecting area 312 at the bottom end of the collecting channel 311. The collecting channel 311 has an outlet opening 314 at the top end, which optionally is covered by an outlet septum 315. The outlet septum 315 is thin enough and contains a slit 316 and has a cracking pressure, which in certain embodiments plays two functions. When fluid is pipetted into the sample loading well 310 through the inlet 313, the outlet septum allows air to leak through the outlet septum. On the other hand, the outlet septum 315 is used to insert a pipette tip to remove fluid after processing. The outlet septum 315 seals when there is no pipetting-action taking place.

Figure 4C:
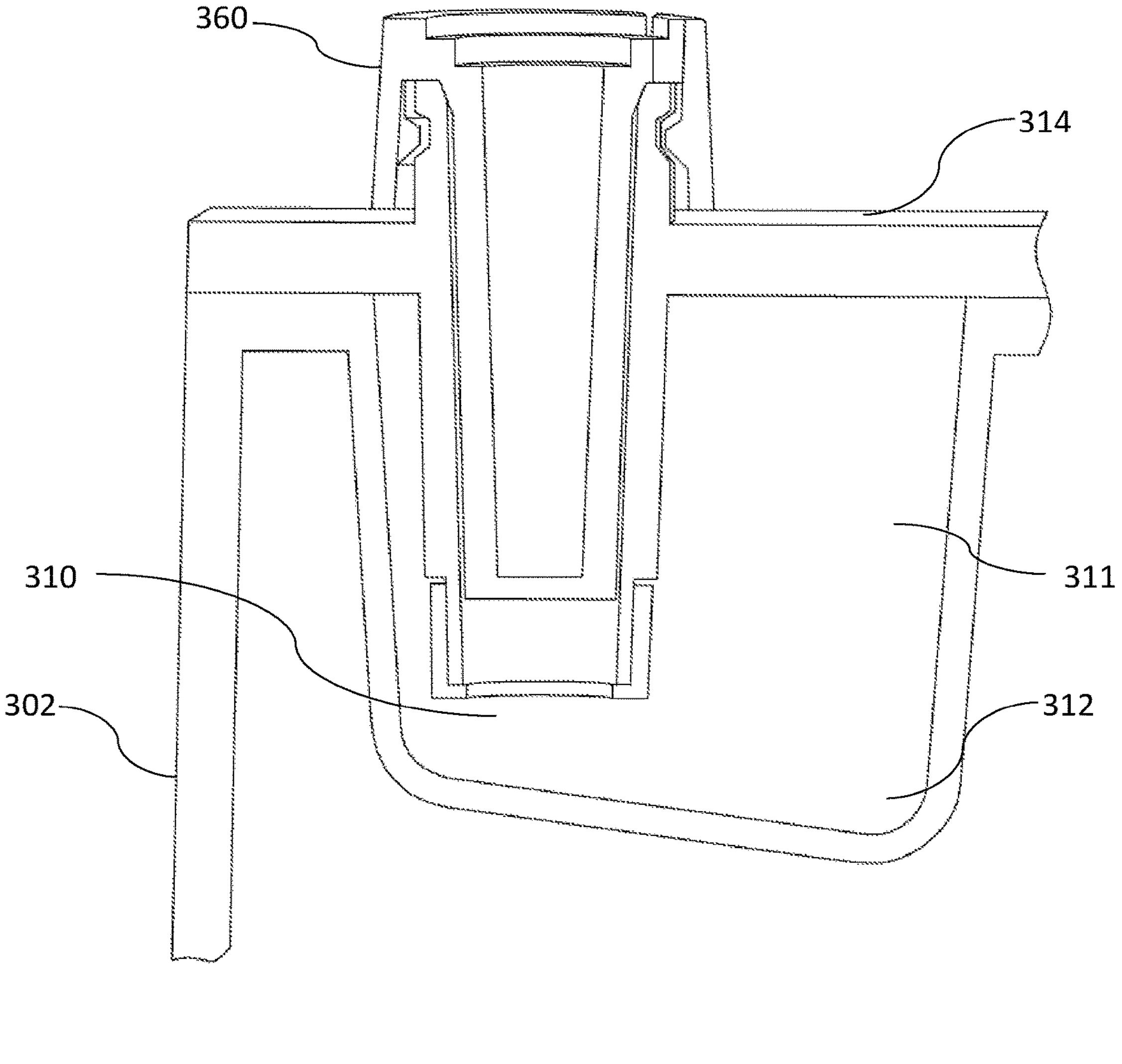
FIG. 4C shows a cross-sectional view of a sample loading well.

FIG. 4C shows a cross-sectional view of the sample loading well of FIG. 4A as shown above along the section plane (a). Referring to FIG. 4C, the bottom of the sample loading well 310 is configured to form a fluid collecting area 312 at the bottom end of the collecting channel 311, with an outlet opening 314 at the top end. As shown in FIG. 4C, in the cross-section along the section plane (a), the sample loading well 310 can be asymmetric, with a deepest portion at the fluid collection area 312. The deepest portion fits a pipette tip so that the pipette tip can reach the deepest portion without touching the sidewalls when the tip is in an aspirate position.

In certain embodiments, the sample loading well 310 is covered by a removable cap to protect contents in the well and prevent cross-contamination. The cap may be made of plastic or other suitable material known in the art.

Figure 5A:
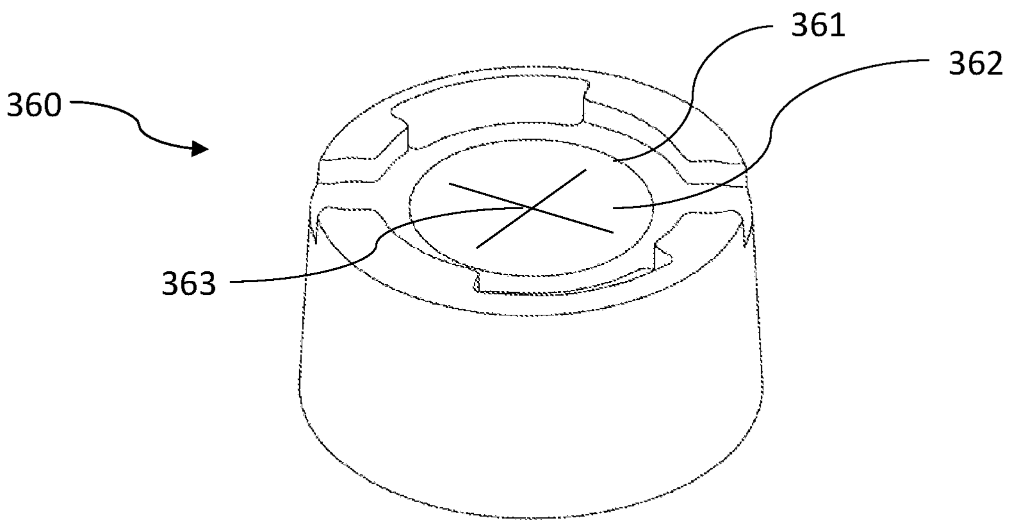
FIG. 5A shows a top perspective view of a removable cap.
Figure 5B:
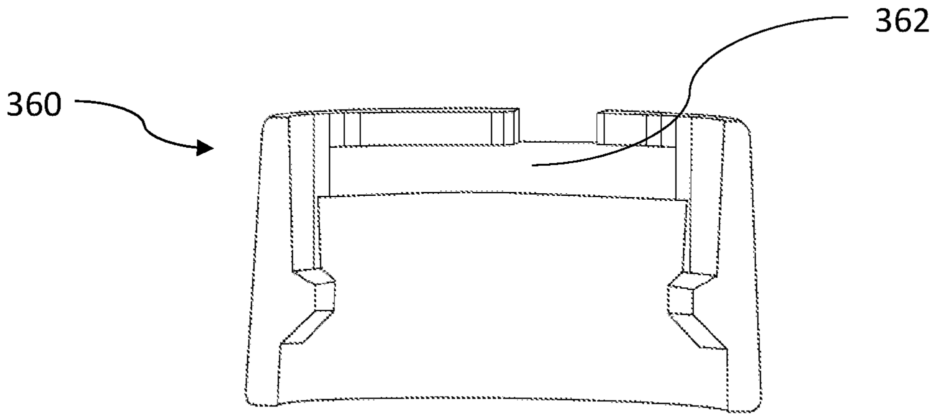
FIG. 5B shows a side, cross-sectional view of a removable cap.

FIGS. 5A and 5B show a top perspective view and a side cross-section view of the cap, respectively, according to one embodiment. Referring to FIG. 5A, the cap includes an inlet 361 for samples to be pipetted into the sample loading well. The inlet 361 is covered by an inlet septum 362. When a pipette tip is inserted into the sample loading well through the inlet 361, the inlet septum 362 seals around the tip, allowing fluid to be pushed and pulled into the well. The inlet septum 362 is thin enough and contains a slit 363 and has a cracking pressure that allows fluid to be pipetted in through the inlet septum, but seals when there is no pipetting-action taking place.

In certain embodiments, the removable cap 360 comprises a plunger 364 that is inserted into the FFPE sample insert.

Figure 5C:
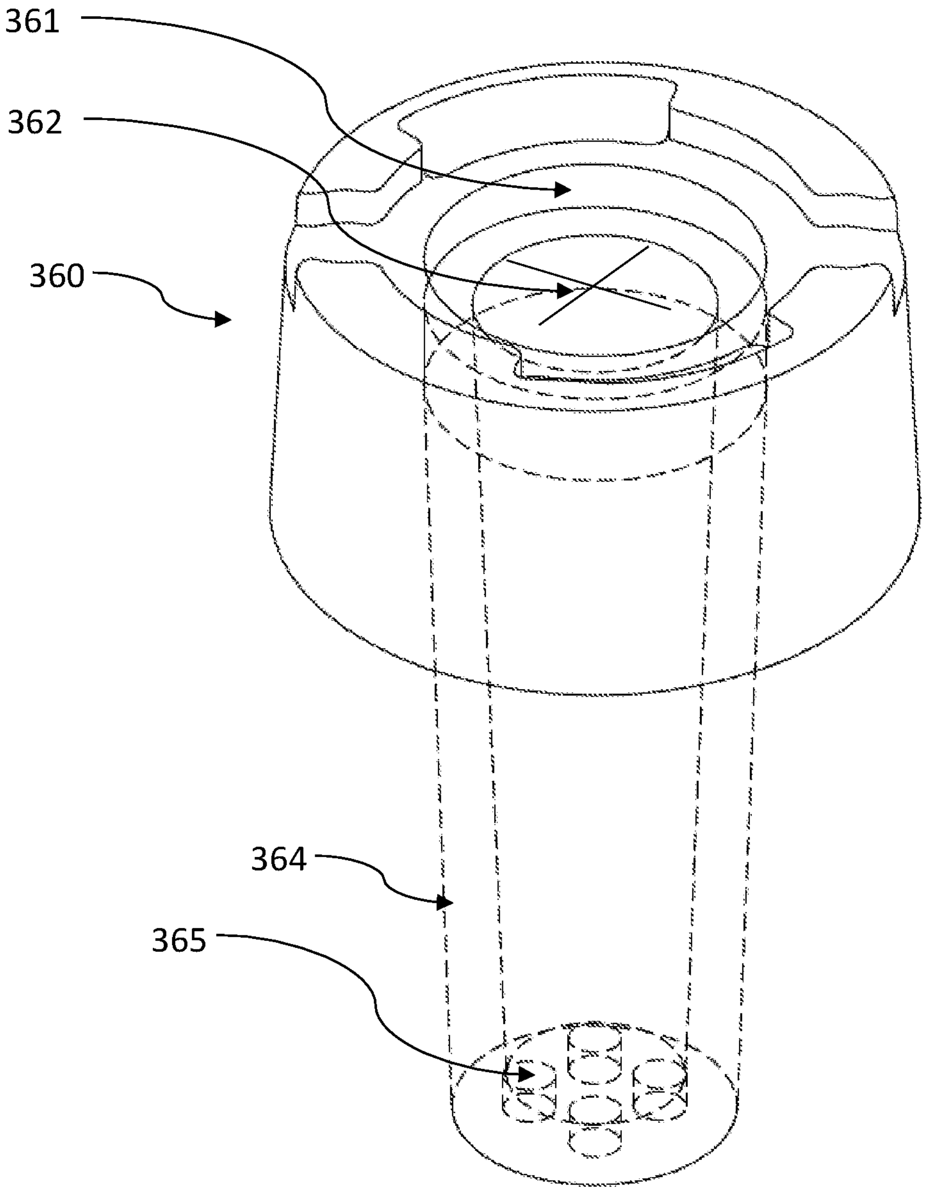
FIG. 5C shows a top perspective view of a cap with a plunger.
Figure 5D:
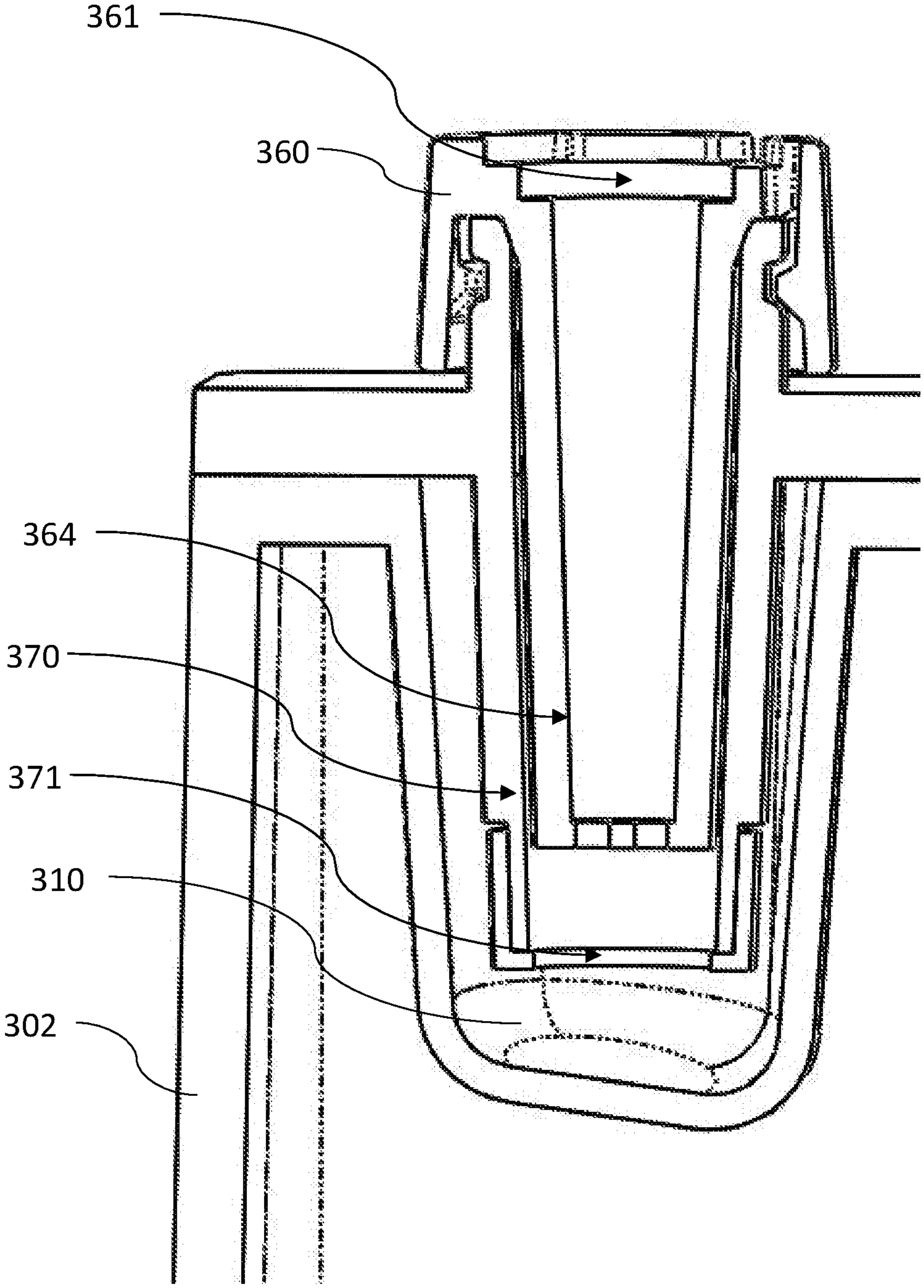
FIG. 5D shows a side, cross-sectional view of a cap with plunger as it is used with an FFPE capture insert.

FIGS. 5C and 5D show a top perspective view and side cross-section view of the removable cap 360 with a plunger 364 according to one embodiment. Referring to FIGS. 5C and 5D, the removable cap 360 has a plunger 364 attached to the cap. In one embodiment, the plunger 364 has a well structure of a cylindrical shape and has a diameter small than the FFPE sample insert 370. Referring to FIG. 5D, in use, a solid FFPE sample is placed in the FFPE sample insert 370 before the removable cap 360 with a plunger 364 is mounted to push the FFPE sample to the bottom of the FFPE sample insert 370. The FFPE sample insert 370 has a mesh filter 371 at the bottom end to prevent the solid FFPE sample from passing the FFPE insert 370 to the sample loading well 310. FFPE lysis buffer is then loaded into the plunger 364 through the inlet 361, which is covered by the inlet septum 362. The FFPE lysis buffer passes through the plunger 364 into the FFPE sample insert 370 via at least one hole 365 (see FIG. 5C) at the bottom of the plunger 364, and then passes into the sample loading well 310 via the mesh filter 371. In some embodiments, the FFPE sample has a density lower than the FFPE lysis buffer, causing the FFPE sample to float on the top of the lysis buffer. As a result, the FFPE sample may stick to the side of the holder and cannot be effectively lysed. The plunger 364 pushes the FFPE sample down to the lysis buffer so that it can be effectively lysed.

Figure 6:
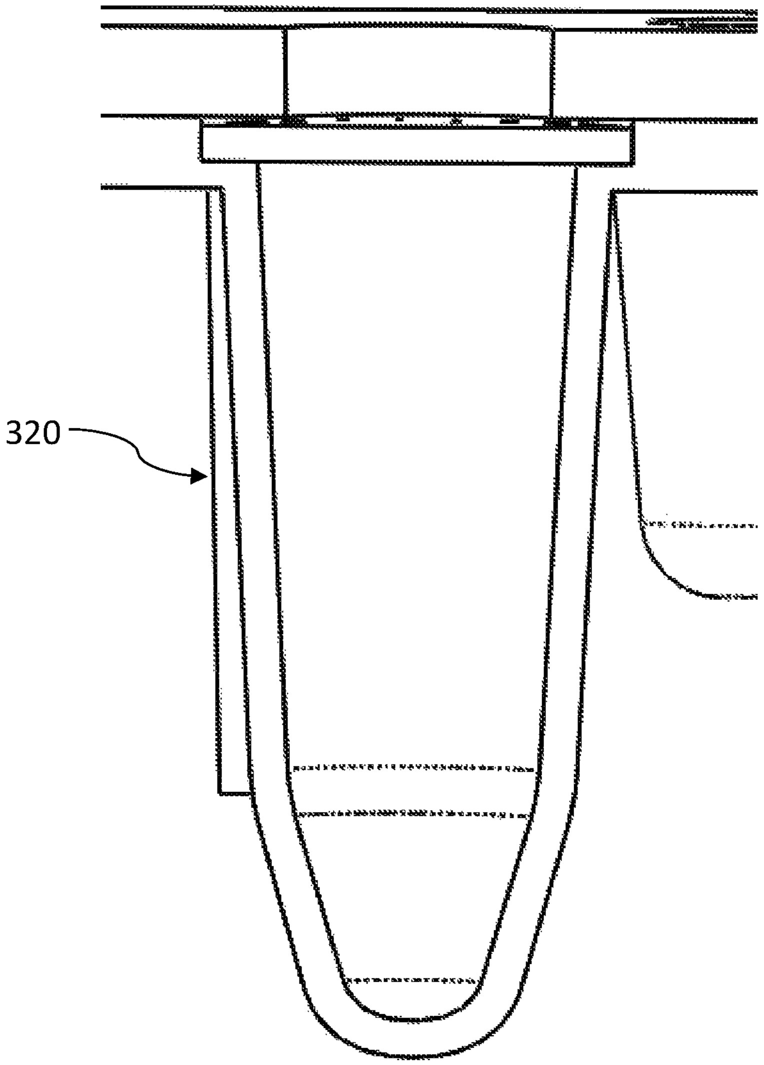
FIG. 6 shows a side, cross-sectional view of a nucleic acid purification well.

FIG. 6 shows a cross-sectional view of a purification well according to an embodiment of the invention. As shown in FIG. 6, purification well 320 is cylindrical with conically tapered bottoms. This shape minimizes dead volume and allows a pipettor to collect all, or nearly all, of the contained reagent. In some embodiments, purification well within sample preparation module may hold the solid phase microparticles (e.g., magnetic nanoparticles). In some embodiments, the system stores solid phase microparticles in suspension, but dry storage may extend shelf life. In either case, solid phase microparticles may require mixing before use either to resuspend microparticles that settle in storage or to disperse a rehydrated suspension.

In some embodiments, the device mixes contents in the purification well using tip mixing. Tip mixing can include one or more cycles of aspiration and redispense of the contents. For example, the tip could be a microtip and aspiration and redispense of the contents may be performed using the microtip. Tip mixing agitates the contents so that different elements of the fluid interact on a small scale. The conical bottoms of the purification wells support agitation and limited rotation of the redispensed contents with a minimum of uninvolved volume. The redispense process uses the kinetic energy of the redispensed fluid to impel fluid agitation. The purification well has a diameter that reduces the effects of capillary forces on mixing. The purification well has a depth greater than its diameter to better contain any splashing. In some embodiments, the depth of the purification well is at least twice its diameter.

While the device operates on other compartments in the sample preparation module primarily from the top, the purification well can also interact with a magnet through its sides and edges (e.g., the bottom). In certain embodiments, when the assay cartridge is loaded into the device and the solid phase microparticles need to be collected, a magnet is pushed up to contact closely to the purification well. The magnet can be controlled to set up a magnetic field that collects and pellets magnetically responsive microparticles on the wall of the purification well. The magnet can be turned off (i.e., to remove the magnetic field) when needed so that the magnetically responsive microparticles can be mixed with other contents in the purification well or be collected by a pipettor. In certain embodiments, when needed, the magnet stays at a home position that is low on the bottom to avoid affecting the solid phase microparticle in the purification well.

In one embodiment, to isolate DNA or RNA from a sample that has been lysed in the sample loading well, proper binding buffer is added to allow DNA or RNA to bind to magnetically responsive microparticles. A magnet is then pushed up to contact closely to the purification well to apply the magnet field and collect the microparticles on one side of the purification well. The liquid is removed using the pipettor system. The magnet field is then removed and the wash buffer is added into the purification well and fully mixed with the microparticles. The magnet field is again applied to collect the microparticles and the wash buffer is removed. Elution buffer is added to the purification well to mix with the microparticles. Purified DNA or RNA is then eluted from the microparticles for downstream application.

Reagent storage wells within sample preparation modules may hold discrete components used in the extraction and purification process, including cell lysis buffer, wash buffer and elute buffer.

Reagent storage wells with sample preparation modules may be of various sizes and shapes. In some embodiments, the reagent storage wells have a filled volume of 100 uL-1000 u. In certain embodiments, the reagent storage wells may be cylindrical with conically tapered bottoms. This shape minimizes dead volume and allows a pipettor to collect all, or nearly all, of the contained reagent. In some embodiments, the bottoms of the reagent storage wells may have a central deepest point, and may be rounded, conical, or pyramidal.

A barrier film may seal the reagent storage wells individually to preserve the reagents and to prevent reagent cross-contamination. In some embodiments, a single barrier film may cover all reagent storage wells. In another embodiment, the reagent storage wells of the sample preparation module may have individual seals. The barrier film may be a multilayer composite of polymer (e.g., rubber) or sticky foil. In some embodiments, the barrier film includes cross cut at the center of each compartment that has both sufficient stiffness and flexibility to cover the opening of the compartments when piercing device (e.g., a microtip) is removed. The barrier film can be a continuous piece spanning all of the reagent wells. In operation, a pipette tip pierces the barrier film from the cross cut to access contents in the reagent storage well. In some embodiments, the manufacturing process may fix the barrier film to the reagent storage well with methods known in the art, e.g., laser welds, heat sealing, ultrasonic welding, induction welding, and adhesive bonding.

In some embodiments, the device uses materials from reagent storage wells in a sequence that is roughly based on the position of the reagent storage wells in the sample preparation module. The device may limit transfers to a single aspiration from each reagent storage well in order to avoid use of material possibly contaminated by an earlier aspiration. The device may first use materials from reagent storage wells nearest the purification well. When removing wastes, the device first deposits its waste materials in empty wells closest to the purification well. The sequencing of well usage may reduce the possibility of contamination. Any drips falling from the pipettor can only fall in wells that the device has already used.

B. PCR Module

In one embodiment, the PCR module comprises an elongated body comprising a proximal end and a distal end, and a plurality of compartments arranged between the proximal end and the distal end, wherein at least one of the compartments is a push well and at least one of the compartments is a PCR well. The push well is where nucleic acid extracted and purified in the sample preparation module is loaded. In certain embodiments, the push well is pre-loaded with a solution mixture including reagents for PCR reaction, e.g., primers, PCR reaction buffer, polymerase and fluorescence dye. The nucleic acid loaded in the push well mixes with the solution mixture, which then flows through a microfluidic channel into the PCR well where PCR reaction is carried out.

Figure 7A:
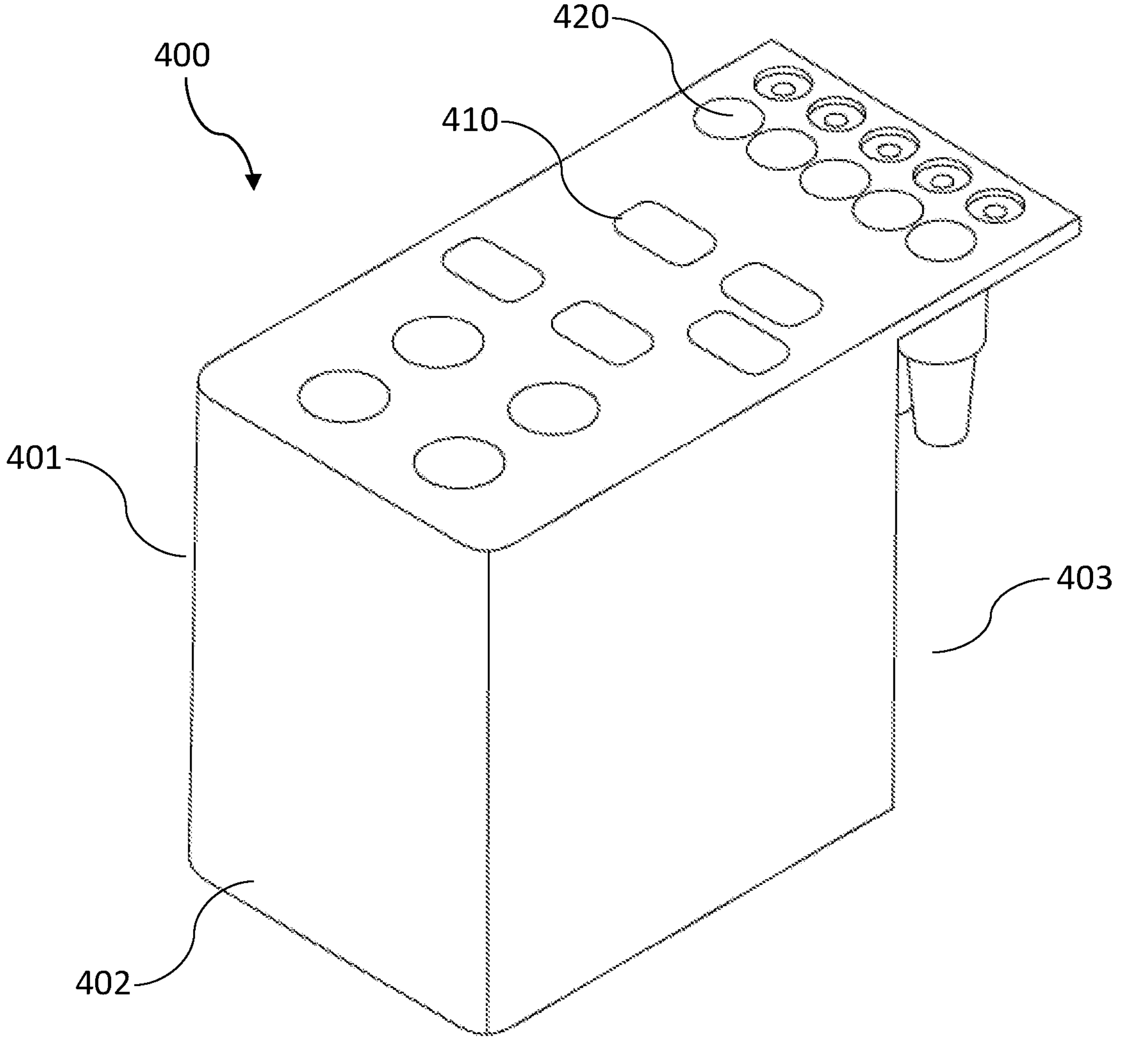
FIG. 7A shows a top perspective view of a PCR module according to an embodiment of the invention.
Figure 7B:
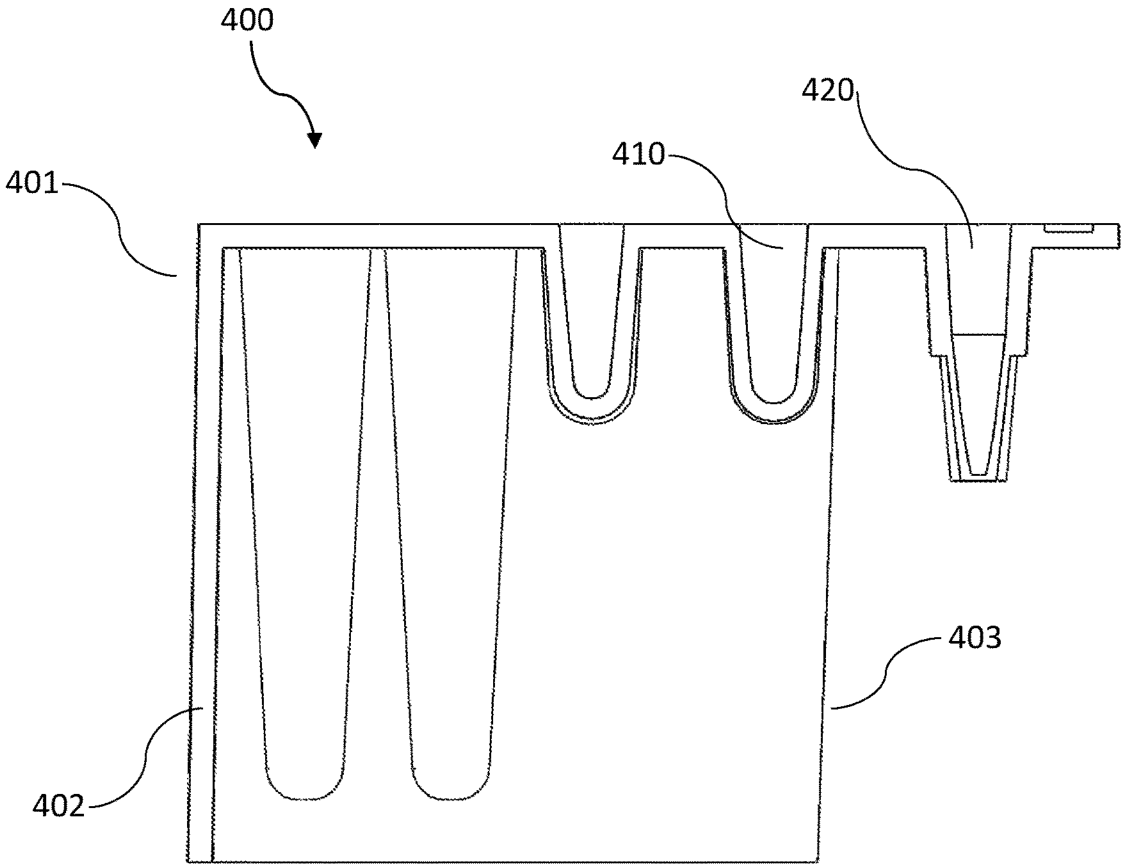
FIG. 7B shows a side, cross-sectional view of the PCR module.

FIGS. 7A and 7B show the top perspective view and a side cross-section view, respectively, of a PCR module according to one embodiment of the invention. Referring to FIGS. 7A and 7B, the PCR module 400 comprises an elongated body 401 formed to include multiple compartments, which may hold fluids (e.g., reagents) and devices (e.g., pipette tips) needed to perform various PCR reactions. Examples of compartments may include one or more push wells 410, one or more PCR wells 420, and one or more pipette tip holders. In certain embodiments, the PCR module 400 can be in the form a monolithic body, and may be formed of plastic (or any other suitable material). In certain embodiments, the PCR module 400 is made by a plastic injection molding process. Alternatively, the PCR module 400 is made by assembling individual components into a rigid framework.

The PCR module 400 can have a proximal end 402 and a distal end 403 at opposite ends of the elongated body 401. The orientation of the compartments defines the top and bottom portion of the PCR module 400. In certain embodiments, compartments can be open at the top and closed on the bottom and sides.

The push well 410 can be of various shape. In one embodiment, the push well 410 is cylindrical with conically tapered bottom. In another embodiment, the push well 410 is generally rectangular.

The PCR well 420 is cylindrical with a conically tapered bottom.

The PCR module 400 has a microfluidic channel that connects the push well 410 and the PCR well 420. In one embodiment, the microfluidic channel connects to the push well 410 through an opening located at the bottom of the push well 410. In one embodiment, the microfluidic channel connects to the PCR well 420 through an opening located at the top of the PCR well 420.

The PCR module 400 may also include a cover (e.g., a barrier film) that is disposed around various compartments and the microfluidic channel, features to facilitate handling (e.g., a half fastener 203), selected reagents and labeling.

As shown in FIGS. 7A and 7B, compartments within a PCR module 400 can be arranged in a generally linear layout, with the pipette tip holder 430 located near the proximal end 402, followed by the push well 410, and the PCR well 420 at the distal end 403. This layout allows simple motion of the dispense system to transfer the fluids among various compartments. Alternatively, the PCR module 400 can take different shape and arrangement of the compartments (e.g., an arc, a single-row linear, or a circle), depending on the overall system design, such as on the number and sequence of operative locations that need access to the individual compartments within a PCR module.

In some embodiments, the top ends of various compartments of a PCR module form openings that align at a common height. In some embodiments, the bottom ends of multiple PCR ends align at a common depth and fit to the receptacles in the thermal cycle module.

In some embodiments, various compartments lack common walls to prevent the creeping of liquids between compartments. This has the benefit of reducing the possibility of contamination between compartments. In some embodiments, the external profile of each compartment closely tracks the cavity internal profile, i.e., the walls of the compartment can be of relatively constant thickness and can be thin compared to the size of the compartment. Such design has the benefits of reducing the amount of material used and hence reducing the manufacturing cost of the module, and improving thermal contact/temperature control of the compartments.

A barrier film may seal the push wells and PCR wells individually to preserve the reagents and to prevent reagent cross-contamination. In some embodiments, a single barrier film may cover all compartments within the PCR module. In another embodiment, the compartments of the PCR module may have individual seals. The barrier film may be a multilayer composite of polymer and foils, and can include metallic foils. In some embodiments, the barrier film includes at least one foil component that has both a low piercing force and sufficient stiffness to maintain an opening in the barrier film once the piercing device (e.g., a pipette tip) is removed. Additionally, the barrier film may be constructed such that no fragments of the foil component are released from the barrier film upon piercing. A suitable material for the barrier film may be stick foil. The barrier film can be a continuous piece spanning all of the push wells and PCR wells. In operation, a pipette tip pierces the barrier film to load purified nucleic acid in the push well. In some embodiments, the manufacturing process may fix the barrier film to the push well and PCR well with methods known in the art, e.g., laser welds, heat sealing, ultrasonic welding, induction welding, and adhesive bonding.

In order to keep the PCR well sealed during thermal cycling, the sample fluid is pushed into the PCR well through a microfluidic channel from an adjacent push well. This prevents cross contamination and evaporation. The sample volume is added to the push well and pressure applied using the pipette tip causes the fluid to flow into the PCR well. In some applications, oil may be pushed after the sample or provide an oil overlay for condensation prevention.

In some embodiments, different types of PCR module may be combined with the sample preparation module depending on the application. Some PCR modules may have multiple PCR wells for thermal cycling. Some PCR wells can be used to perform the reverse transcription reaction or any other thermal process prior to the polymerase chain reaction. Extra reagent storage wells can be added to modules requiring additional thermal cycling wells.

C. Marking and Packaging

Assay cartridges may include marking elements to transfer information. Marking may include human readable information such as text or illustrations. Marking may also include machine readable information in any of a variety of forms such as barcodes, dot codes, radio frequency identification tags (RFID) or direct reading electronic memory. In some embodiments, each module of an assay cartridge includes a barcode (e.g., on the side of the sample preparation module and the side of the PCR module). The marking may include information about module type, manufacturing information, serial numbers, expiration dates, use directions, etc.

Prior to loading on the device, assay cartridges may be stored in transport boxes. Sample preparation modules and PCR modules may be stored in one package or in separate packages. Typically, a transport box retains several modules in common orientation, grouped for easy grasping of several at a time to load. In some embodiments, transport boxes include a supporting base, labeling, and a clamshell lid to protect the modules during handling. Manufacturing processes useful for producing transport boxes include at least plastics thermoforming and plastics injection molding.

Cartridge Loading Unit

In some embodiments, the assay cartridges can be loaded into the device through a cartridge loading unit. The cartridge loading unit serves as an area for loading and temporary storage of assay cartridges in the system. In use, assay cartridges can be loaded into the system at the cartridge loading unit without interrupting normal device operation, such as the processing of the assay cartridges loaded earlier. After loading, the cartridge loading unit may read marking elements, such as a barcode, that are attached to the loaded assay cartridges. In certain embodiments, a barcode reader attached to the dispense system is used to read the barcode. In certain embodiments, a barcode reader installed in the loading channel is used to read the barcode. A proper protocol may then be launched to direct the processing of the sample.

Figure 8A:
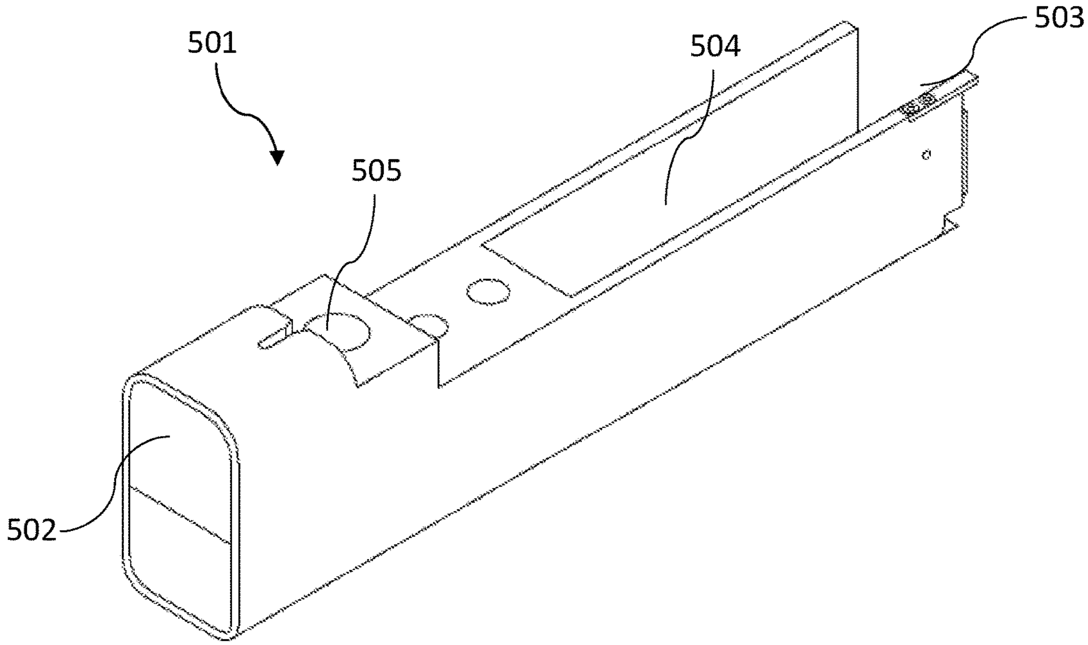
FIG. 8A shows a top perspective view of a cartridge carriage according to an embodiment of the invention.
Figure 8B:
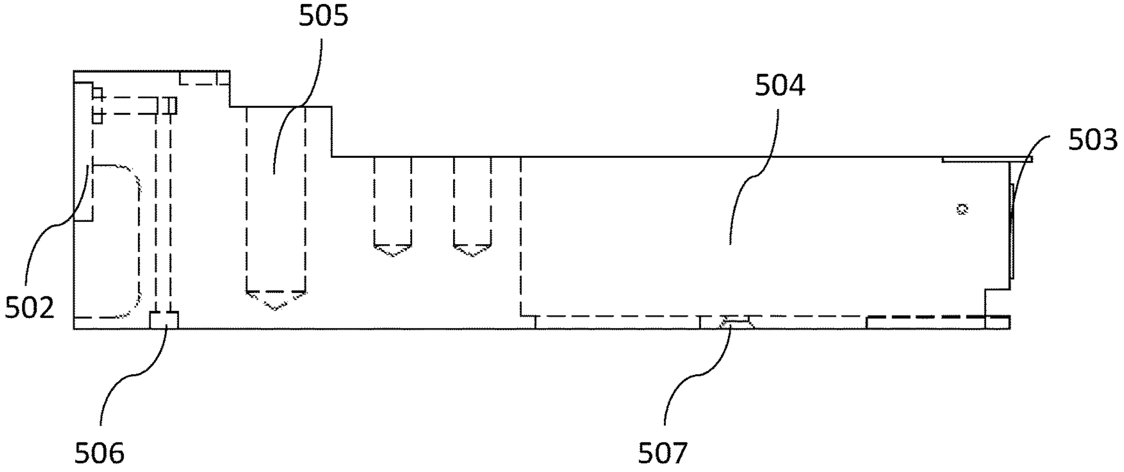
FIG. 8B shows a side, cross-sectional view of a cartridge carriage according to an embodiment of the invention.

In some embodiments, the cartridge loading unit comprises a plurality of cartridge loading lanes accommodating cartridge carriages, each of which receives an assay cartridge. FIG. 8A shows a top perspective view of a cartridge carriage according to an embodiment of the invention. FIG. 8B shows a side cross-sectional view of the cartridge carriage of FIG. 8A. Referring to FIGS. 8A and 8B, the cartridge carriage 501 has an elongated body having a proximal end 502 and a distal end 503. The cartridge carriage 501 can include a storage location near the distal end 503 comprising a cavity 504 configured to hold assay cartridge. In some embodiments, the cartridge carriage 501 includes at least one sample vial holder 505. In use, the sample vial holder 505 may receive a vial of sample, which can be added to the assay cartridge loaded in the cartridge carriage 501, either by a user or by the device.

Figure 8C:
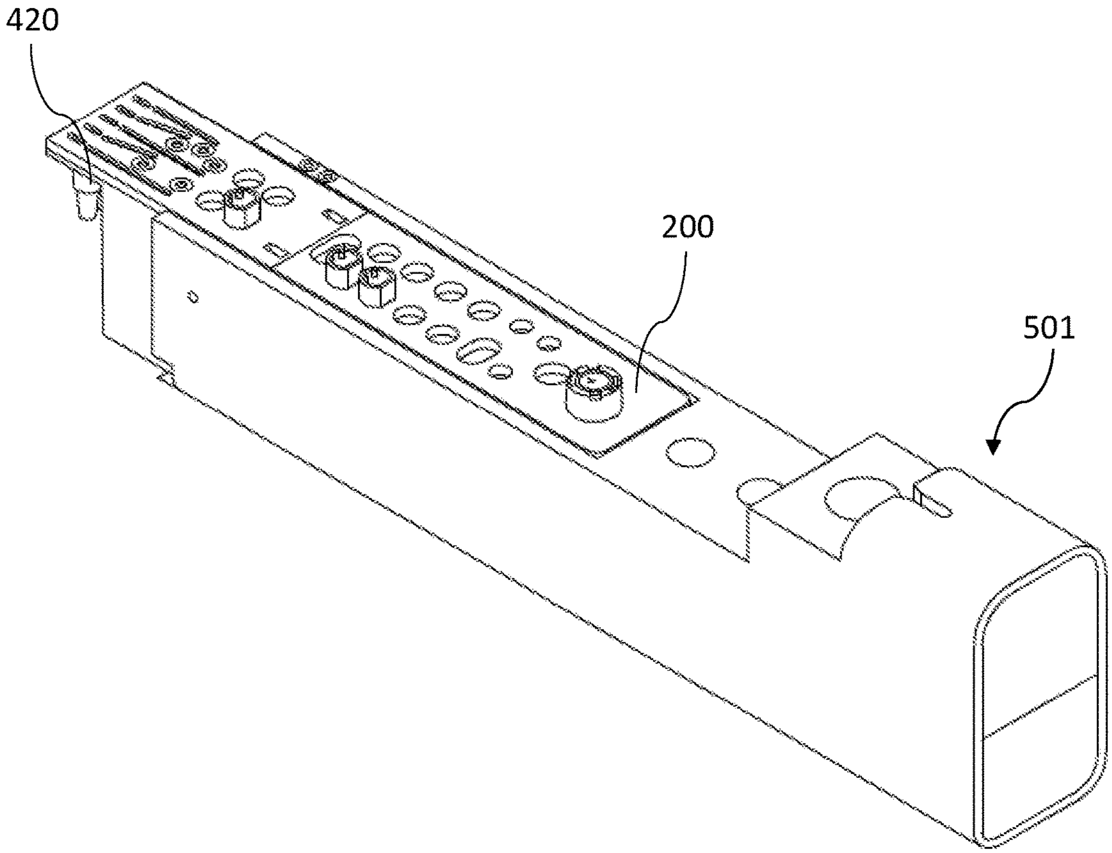
FIG. 8C shows a top perspective view of a cartridge carriage with an assay cartridge loaded in processing lane.
Figure 8D:
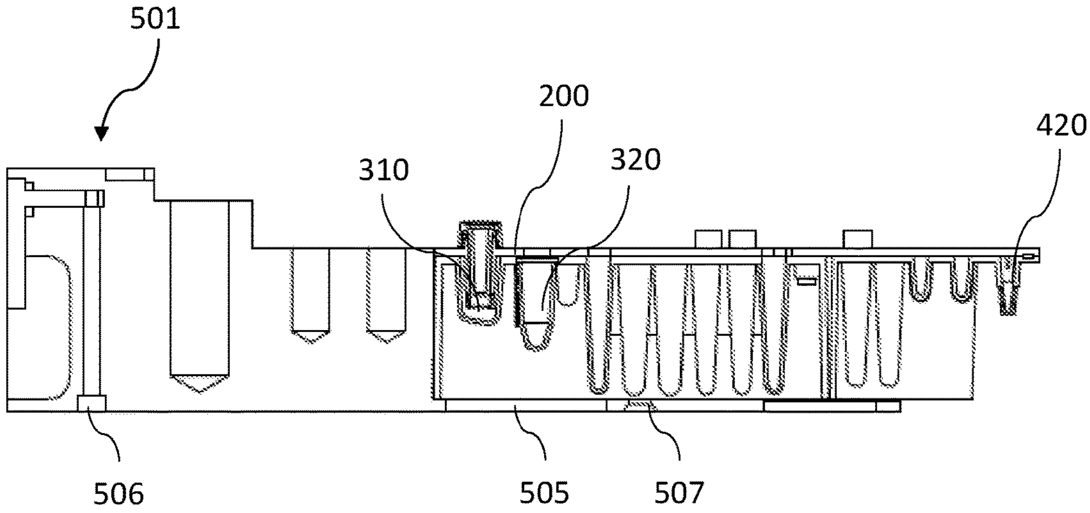
FIG. 8D shows a side, cross-sectional view of a cartridge carriage with an assay cartridge loaded in processing lane.

FIGS. 8C and 8D shows a top perspective view and a side cross-section view, respectively of a cartridge carriage according to an embodiment of the invention, with an assay cartridge loaded in the cartridge carriage. Referring to FIGS. 8C and 8D, the assay cartridge 200 can be loaded into the cavity of the cartridge carriage 501. In one embodiment, the PCR wells 420 of the assay cartridge 200 are not loaded into the cavity. This design allows the PCR wells 420 to be received in the receptacles of the thermal cycler module. In one embodiment, the cartridge carriage 501 has a structure that secures the assay cartridge into the appropriate position in the cavity 504. In one embodiment, the structure includes a groove located at the distal end of the cavity that fits a groove runner at the bottom of the assay cartridge. In one embodiment, the cartridge carriage 501 has an opening 505 at the bottom wall. The opening 505 allows the device to interact with the sample loading well 310 and the purification well 320 of the assay cartridge 200 through its sides and edges. For example, when the assay cartridge 200 is loaded into the device, a magnet is positioned to contact closely to the side of the purification well 320, which assists to pellet the magnetically responsive microparticles in the purification well 320. For another example, a heater can be positioned close to sample loading well 310 to assist the lysis of a sample, e.g., a FFPE sample.

In some embodiments, the cartridge carrier 501 includes a proximal fix tab 506 and a distal fix tab 507 that secures the cartridge carrier 501 in appropriate location in the device when cartridge-loaded carrier is loaded into the device. In one embodiment, the proximal fix tab 506 and the distal fix tab 507 are designed such that the cartridge carrier 501 can be removed from the device when a user pulls the cartridge carrier out of the device.

Dispense System

In some embodiments, the systems disclosed herein use a dispense system including a XYZ gantry with a pipettor to perform a variety of functions, such as transferring a reagent between compartments in assay cartridges.

Figure 9A:
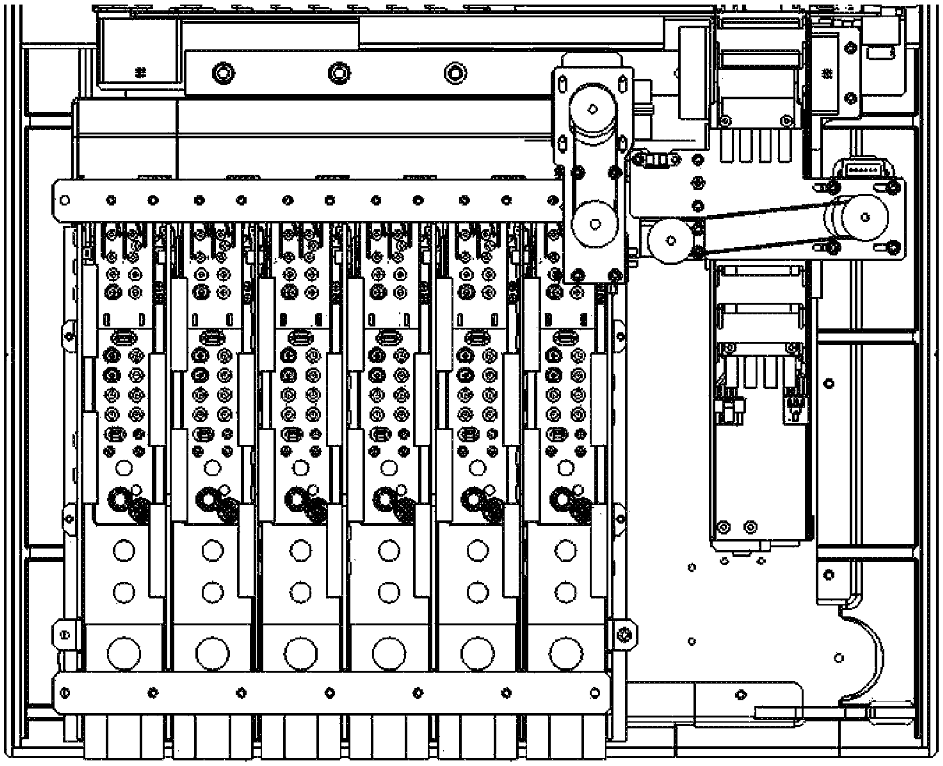
FIG. 9A shows a top plan view of a dispense head according to an embodiment of the invention.
Figure 9B:
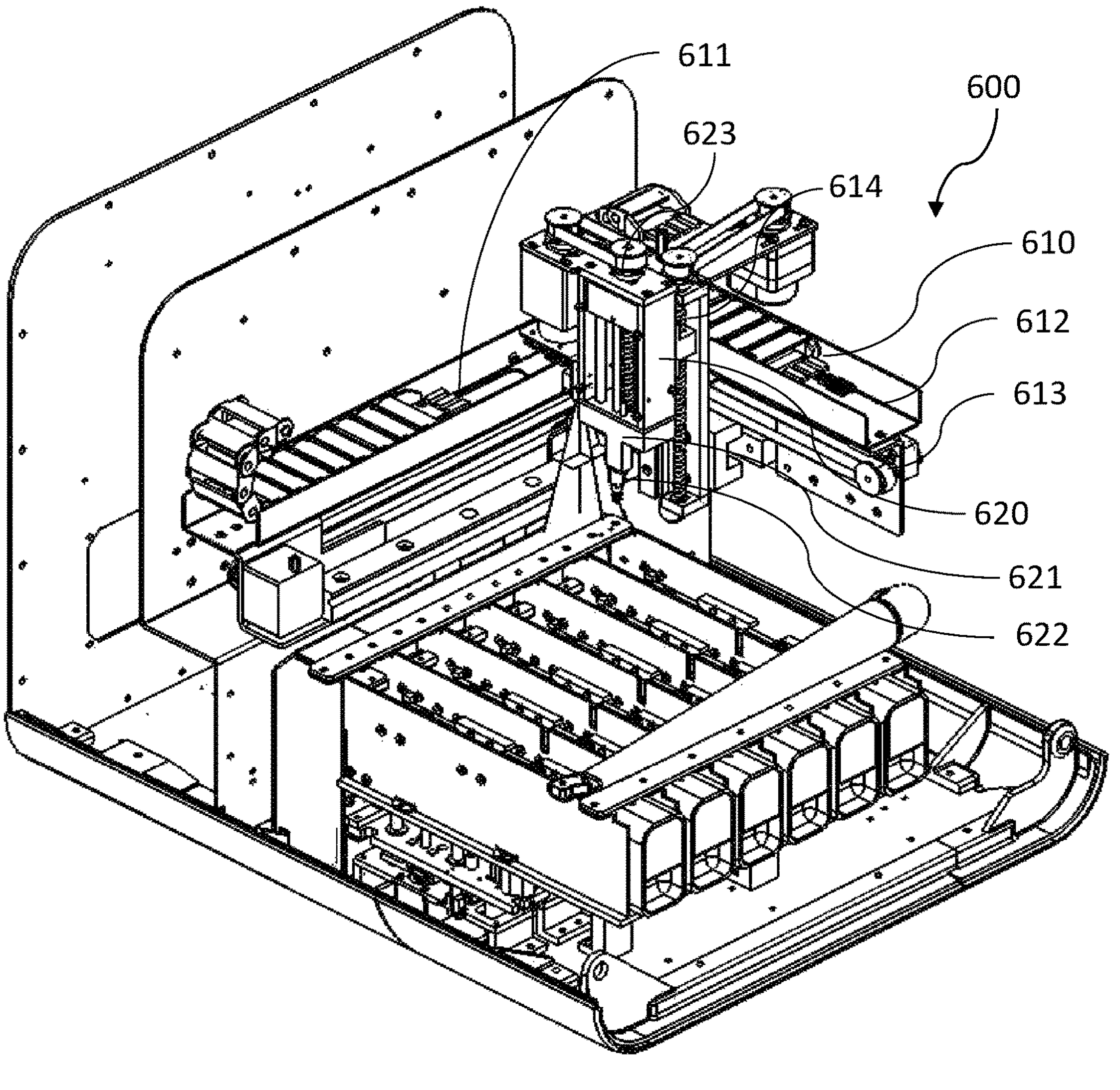
FIG. 9B shows a top perspective view of a dispense head according to an embodiment of the invention.

FIGS. 9A and 9B show a top view and perspective view of a dispense system according to an embodiment of the invention, respectively. Referring to FIG. 9B, the dispense system 600 includes a XYZ gantry 610 and a pipette pump assembly (pipettor) 620. The XYZ gantry 610 has an "L" shape structure on the horizontal plane and is configured to control the three-dimensional movement of the pipettor 620. In one embodiment, the XYZ gantry 610 has an X-axis track 611 that is perpendicular to the axes of the cartridge-loading lane. The XYZ gantry 610 also has a Y-axis track 612 that is perpendicular to the X-axis track (i.e., parallel to the axes of the cartridge-loading lane). In one embodiment, the X-axis track 611 has a fixed location in the device while the Y-axis track 612 is attached to the X-axis track 611 and is freely movable along the X-axis track 611. The pipettor 620 is attached to and freely movable on the Y-axis track 612. In one embodiment, the dispense system 600 uses at least one motor coupled to a pulley system 613 to control the location of the pipettor. In one embodiment, the motor is attached to the gantry near one terminus of a track. The pulley system 613 contains a drive pulley that coupled to the motor and an idler pulley attached to the gantry near the opposite terminus of the track. A timing belt substantially parallel to the track may connect the drive pulley to the idler pulley. Rotation of the motor drives the timing belt and adjusts the separation between the drive pulley and the idler pulley, thus moves the pipettor along the track. The combination movement of the Y-axis track 612 and the pipettor 620 allows the pipettor 620 to be positioned appropriately on a horizontal plane. Alternatively, the XYZ gantry 610 may have any suitable structure capable of directing the movement of the pipettor 620 such as a rotary transport or an articulated arm.

In one embodiment, the pipettor 620 contains a pipettor carriage 621 that supports a pipettor head 622. In one embodiment, the XYZ gantry 610 also includes an elevator 614 that can raise and lower the pipettor 620 as required for pipetting, mixing, resuspension, and transfer. In one embodiment, the pipettor 620 also contains a lift 623 that can raise and lower the pipettor head 622. This allows the fine tuning of location of the pipettor head as required for pipetting, mixing, resuspension and transfer without using the XYZ gantry 610 to move the pipettor 620.

The pipettor 620 can be used to transfer liquids from one location to another throughout the system. The pipettor 620 may transfer liquids that include patient samples stored in sample vials, which may include serum, plasma, whole blood, urine, feces, cerebrospinal fluid, saliva, tissue suspensions, and wound secretions. The pipettor 620 may also transfer liquids, such as reagents, between compartments in the assay cartridge 200.

In order to reduce contamination, the pipettor 620 typically uses disposable pipette tips to contact liquids. A pipettor mandrel may act as the point for the attachment of disposable pipette tips to the pipettor. Attachment can be held in place actively by a gripper or held in place passively by friction between the inner surface of the pipette tip and the outer surface of the pipettor mandrel.

In one embodiment, the pipettor 620 has a pipette pump that is specifically constructed to accurately aspirate and dispense fluids within a defined range of volumes, e.g., 1-20 uL, 10-200 uL 200-1000 uL.

Thermal Cycler Module

In some embodiments of the invention, the system disclosed herein comprises a thermal cycler module used to amply a specific nucleic acid sequence through PCR.

As disclosed above, PCR or "Polymerase Chain Reaction" is a process used to amplify DNA through repeated cycles of enzymatic replication followed by denaturing the DNA duplex and formation of new DNA duplexes, i.e., thermal cycles. Denaturing and annealing of the DNA duplex may be performed by altering the temperature of the DNA amplification reaction mixture. Reverse transcription PCR refers to a process that converts mRNA into cDNA before DNA amplification. Real time PCR refers to a process in which a signal (e.g., fluorescence) that is related to the amount of amplified DNA in the reaction is monitored during the amplification process.

In certain embodiments, a thermal cycle can refer to one complete amplification cycle, in which a sample moves through a time versus temperature profile, also known as a temperature profile, that includes: heating the sample to a DNA duplex denaturing temperature, cooling the sample to a DNA annealing temperature, and exciting the sample with an excitation source while monitoring the emitted fluorescence. A typical DNA denaturing temperature can be about 90° C. to 95° C. A typical DNA annealing temperature can be about 50° C. to 70° C. A typical DNA polymerization temperature can be about 68° C. to about 72° C. The time required to transition between these temperatures is referred to as a temperature ramping time. Ideally, each thermal cycle will amplify a target sequence of nucleic acid by a factor of two. In practice, however, amplification efficiency is often less than 100%.

In some embodiments of the invention, the system disclosed herein includes a PCR subsystem that takes a prepared PCR well and performs a complete real-time PCR analysis, thermal cycling the sample multiple times, and reporting the intensity of emitted fluorescent light at each cycle. In certain embodiments, the PCR subsystem comprises a thermal cycler module, one or more PCR wells and an optic module.

As noted supra, a prepared PCR well may contain RNA or DNA isolated from a sample, target sequence specific primers and probes, a "master" mix that includes nucleotide monomers and enzymes necessary for synthesis of new DNA strands. Total fluid volume contained in the PCR well is small (typically 40 μL to 50 μL) to facilitate rapid heat transfer.

Figure 10A:
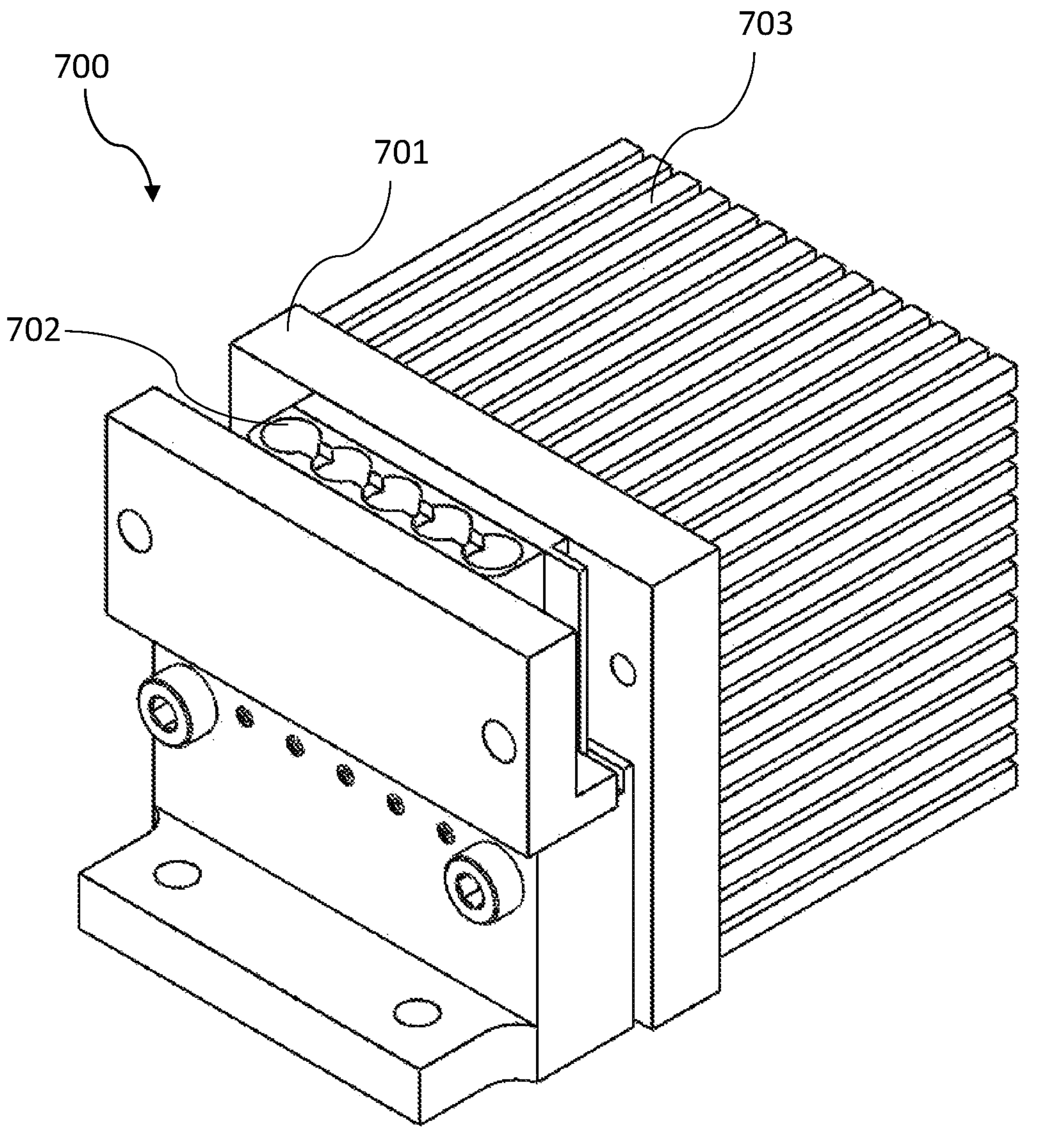
FIG. 10A shows a top perspective view of a thermal cycler module according to an embodiment of the invention.
Figure 10B:
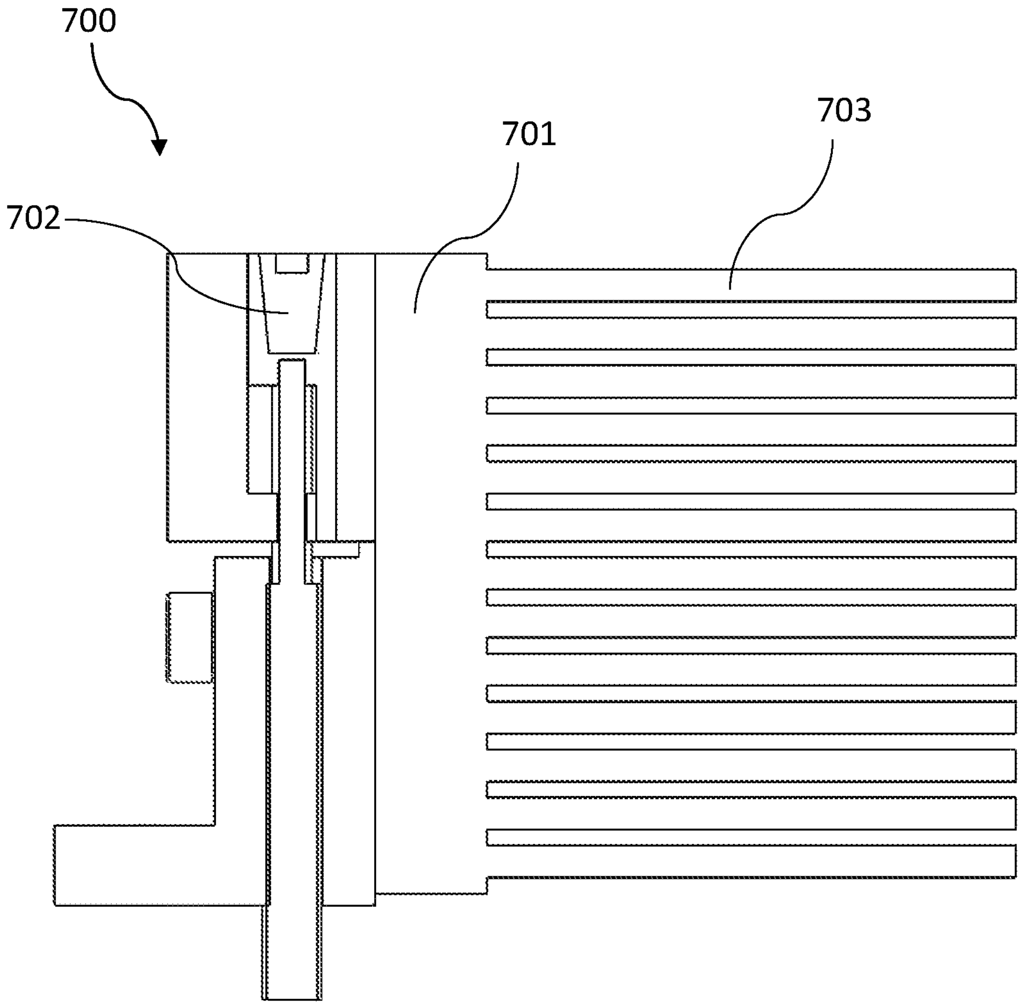
FIG. 10B shows side, cross-sectional view of the thermal cycler module.

FIG. 10A shows a top perspective view of a thermal cycler module according to an embodiment of the invention. FIG. 10B shows a side cross-sectional view of the thermal cycler module of FIG. 10A. Referring to FIGS. 10A and 10B, the thermal cycler module 700 comprises a thermal block 701 with a substantially planar thermal mass for transferring thermal energy, and a receptacle 702 for forming a thermal contact surface with a PCR well. The thermal block 701 may be composed of a highly thermally conductive material such as copper, copper alloy, aluminum, aluminum alloy, magnesium, gold, silver, or beryllium. The thermal block 701 may have a thermal conductivity of about 100 W/mK or greater and a specific heat of about 0.30 kJ/(kg·K) or less. In some embodiments, the thermal block 701 has a thickness between about XX inches and about XX inches. The thermal block 701 can also comprise a heating element that provides the heat that is transferred to the PCR well. The heating element can be a thin film heater affixed to the back surface of the planar thermal mass, although other heat sources such as resistance heaters, thermoelectric devices, infrared emitters, streams of heated fluid, or heated fluid contained within channels that are in thermal contact with the thermal block may also be used. The thermal block may also include one or more temperature sensors that are used in conjunction with a controller to control the temperature of the thermal block by, for instance, a proportional-integral-derivative (PID) loop. These temperature sensors may be imbedded in the thermal block. The receptacle may comprise an optical aperture, where the optical aperture is positioned to permit optical communication through optical fibers to the interior of the receptacle.

In certain embodiments, the thermal cycler module 700 may have a plurality of heat transfer fins 703, which facilitates the release of heat from the thermal block 701. The receptacle 702 may have any suitable characteristics necessary to secure the PCR well and ensure good thermal contact with it. For example, in some embodiments, the walls of the conical receptacle 702 have an angle of about 1 degree to about 10 degrees, an angle of about 4 degrees to about 8 degrees, or an angle of about 6 degrees. The decreasing internal radius of the receptacle ensures that as the PCR well that is pressed into the receptacle 702 the exterior of the PCR well is brought into intimate contact with the interior of the receptacle 702. The receptacle 702 can comprise a frustum of a conical shape and having an upper opening and a lower opening. The receptacle 702 is affixed to the front surface of the thermal block 701. The upper opening allows for insertion of the PCR well. The lower opening acts as an optical window for the optics assembly (as disclosed infra).

Optic Module

The systems of the present disclosure can also include an optic module responsible for exciting the dyes in the assay and detecting the fluorescence emitted at each PCR cycle. Both excitation and emission can occur over a range of wavelengths. Light used to excite the fluorescent dyes can, for example, range from 400 nm to 800 nm. The detector used to measure light emitted form the dyes can, for example, be sensitive to light ranging from 400 nm to 800 nm. In some embodiments, the optical module can detect a plurality of emitted wavelengths from the PCR well and to perform the detection asynchronously across multiple PCR wells. In certain embodiments, up to 5 different dyes can be detected asynchronously among up to 30 different PCR wells.

The optical module includes hardware and software components from the light sources through to the detection on the CCD camera. Typically, the optical module includes at least the following components: an excitation light source, assemblies for directing excitation light to the PCR wells, assemblies for directing light emitted by fluorescent dyes within the PCR wells to a detector, and one or more detectors for measuring the emitted light.

The excitation light source can be lasers (including fixed-wavelength lasers and tunable lasers) and LEDs (including single wavelength LEDs, multi-wavelength LEDs and white LEDs). In some embodiments, the light from the light source is passed through filters (e.g., multibandpass filter) to remove light that is outside of the nominal wavelength range before being directed to the PCR wells.

The light from the light source can be directed to individual excitation optical fibers, which then direct the excitation light to individual PCR wells. In some embodiments, an assembly of 30 excitation optical fibers is used to supply excitation light to each of 30 PCR wells. A variety of optical fibers can be used to carry the excitation light. In some embodiments, the optical fibers are about 200 um in diameter. Excitation optical fibers carrying the excitation light terminate in the excitation optics assembly of the thermal cycler module, which is described above.

Light emitted from the PCR wells as a result of exposure to the excitation light is collected by the emission optics assembly of the thermal cycler module, which is described above. In some embodiments, the emitted light is directed to the input end of an emission optical fiber, which subsequently directs emitted light to a detector.

In some embodiments, the detector can be a spectrometer. The spectrometer may be a multi-channel or an imaging spectrometer, which permits simultaneous reading of multiple optical fibers and reduce the need for switching. The spectrometer can include a multi-bandpass filter between the output terminus of the emission optical fibers and the detector to selectively remove emission excitation wavelengths. In some embodiments, the detector may be a single photo-diode, photomultiplier, channel photomultiplier, or similar device equipped with an appropriate optical filter, which can be a set of optical filters or a tunable filter.

Figure 11:
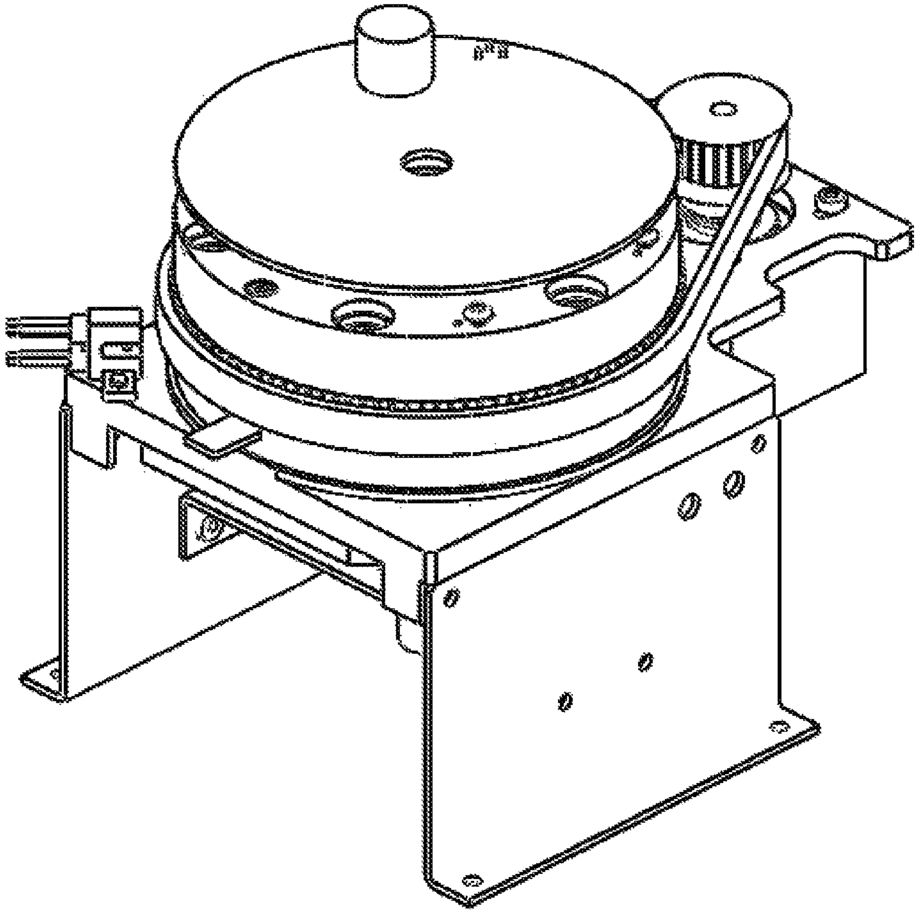
FIG. 11 shows a top perspective view of an optics module according to an embodiment of the invention.

FIG. 11A shows a top perspective view of an optics module according to an embodiment of the invention. Referring to FIG. 11A, the optical module contains a rotary plate that includes multiple filters each for a different wavelength. The filters are arranged on a circle from the center of the rotary plate. The rotary plate is stacked on an optical fiber plate where one terminus of each optical fiber is attached. The optical module also contains a motor coupled to a drive pulley connected to the rotary plate through a belt. Rotation of the motor drives the belt to rotate the rotary plate. The termini of the optical fibers are arranged on a circle matching the one in the rotary plate so that when the rotary plate is rotated the filters can align with the optical fiber termini. This design allows asynchronous detection of fluorescent signals from multiple PCR wells. For example, the rotary plate can contain five filters, each for detection of a different dye. The optical fiber plate contains termini of 30 optical fibers, each for a different PCR well. When the rotary plate rotates above the optical fiber plate, the filters can align with termini of 5 optic fibers. As a result, excitation light is send to the 5 PCR wells, the fluorescent signal from the 5 PCR wells are received. Then the motor drives the rotation of the rotary plate so that the filters align with the next 5 termini. When the rotary plate completes one full circle, the fluorescent signals from all 30 PCR wells can be detected.

EXAMPLE 1

The following is an example of detecting a target nucleic acid using a device disclosed herein.

A 15 um BRAF Wild Type FFPE DNA reference standard scroll (Horizon Discovery, cat# HD266) was used as the sample input. The scroll was inserted into the sample loading well 310 of a sample preparation module 300 as illustrated in FIG. 3A, which was coupled to a PCR module 400 (FIG. 7A). The sample loading well 310 was capped with a removable cap 360 with a plunger 364 (FIG. 5C) and loaded onto the device 100 (FIG. 1A). The sample loading well 310 was preloaded with an FFPE DNA deparafinization (DP) solution (MagBio Genomics, HighPrep™ FFPE Tissue DNA Kit). To extract the DNA from the scroll, the sample loading well 310 was incubated at 65° C. for 15 min. The DP solution was then removed from the sample loading well 310 and replaced with digestion buffer (MagBio Genomics, HighPrep™ FFPE Tissue DNA Kit) and Protease K solution. The solution was incubated at 55° C. for 45 min.

The lysate was then transferred into the purification well 320 (see FIGS. 3A and 3B) which was preloaded with the magnetic beads (Nvigen) in DNA binding buffer (MagBio Genomics, HighPrep™ FFPE Tissue DNA Kit) and incubated at room temperature for 10 min. Magnet force was applied to collect the beads onto the side of the purification well 320, and the liquid was removed from the purification well 320.

The beads were washed once with wash buffer 1 (MagBio Genomics, HighPrep™ FFPE Tissue DNA Kit) and twice with wash buffer 2 (MagBio Genomics, HighPrep™ FFPE Tissue DNA Kit). The beads were air dried and eluted with 50 uL elution buffer (MagBio Genomics, HighPrep™ FFPE Tissue DNA Kit).

The purified DNA was then transferred to a push well 410 (FIG. 7A) that was loaded with the PCR supmermix, including the hotstart PCR polymerase, dNTP and buffer with PCR primer/probe designed to target house-keeping GUSB gene, and loaded into the PCR well. Oil was then loaded on top of the PCR mix to prevent evaporation. PCR started with denaturation at 95° C. for 3 min, followed by 40 cycles of 95° C. for 20 s and 60° C. for 45 s. Fluorescence data was collected at the 60° C. annealing temperature. The collected fluorescence signal was plotted vs cycle number. The Ct value for the run is around 22, which is comparable to the result from manual prep.

The previous description provides exemplary embodiments only, and is not intended to limit the scope, applicability, or configuration of the disclosure. Rather, the previous description of the exemplary embodiments will provide those skilled in the art with an enabling description for implementing one or more exemplary embodiments. It is understood that various changes may be made in the function and arrangement of elements without departing from the spirit and scope of the invention. Several embodiments were described herein, and while various features are ascribed to different embodiments, it should be appreciated that the features described with respect to one embodiment may be incorporated within other embodiments as well. By the same token, however, no single feature or features of any described embodiment should be considered essential to every embodiment of the invention, as other embodiments of the invention may omit such features.

Specific details are given in the previous description to provide a thorough understanding of the embodiments. However, it will be understood by one of ordinary skill in the art that the embodiments may be practiced without these specific details. For example, circuits, systems, networks, processes, and other elements in the invention may be shown as components in block diagram form in order not to obscure the embodiments in unnecessary detail. In other instances, well-known circuits, processes, algorithms, structures, and techniques may be shown without unnecessary detail in order to avoid obscuring the embodiments.

Also, it is noted that individual embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process may be terminated when its operations are completed, but could have also included additional steps or operations not discussed or included in a figure.

Furthermore, not all operations in any particularly described process may occur in all embodiments. A process may correspond to a method, a function, a procedure, a subroutine, a subprogram, etc. When a process corresponds to a function, its termination corresponds to a return of the function to the calling function or the main function.

Furthermore, embodiments may be implemented, at least in part, either manually or automatically. Manual or automatic implementations may be executed, or at least assisted, through the use of machines, hardware, software, firmware, middleware, microcode, hardware description languages, or any combination thereof. When implemented in software, firmware, middleware or microcode, the program code or code segments to perform the necessary tasks may be stored in a machine readable medium. A processor(s) may perform the necessary tasks.

While detailed descriptions of one or more embodiments have been give above, various alternatives, modifications, and equivalents will be apparent to those skilled in the art without varying from the spirit of the invention. Moreover, except where clearly inappropriate or otherwise expressly noted, it should be assumed that the features, devices, and/or components of different embodiments may be substituted and/or combined. Thus, the above description should not be taken as limiting the scope of the invention. Lastly, one or more elements of one or more embodiments may be combined with one or more elements of one or more other embodiments without departing from the scope of the invention.

What is claimed is:

1. A sample preparation module for an assay cartridge used in a PCR-based molecular diagnostic device, said sample preparation module comprising an elongated body which comprises a sample loading well of an asymmetric shape where a sample is loaded before nucleic acid is extracted from the sample, said PCR-based molecular diagnostic device comprising an automatic dispense system to transfer the sample using a pipette, wherein the sample loading well comprises

- a generally vertical wall around the sample loading well,
- a tilted cone shape bottom having a deepest portion,
- a sample loading well inlet covered by a removable cap, and
- a sample collecting channel having a sample loading well outlet at its top end and a fluid collecting area at its bottom end,
- wherein the removable cap has a cap inlet covered by a cap inlet septum having an inlet slit,
- wherein the sample loading well outlet is covered by a sample loading well outlet septum having an outlet slit,
- wherein the fluid collecting area is at the deepest portion of the bottom,
- wherein the pipette is capable of adding the sample to the sample loading well through the sample loading well inlet, and
- wherein the pipette is capable of collecting the nucleic acid from the fluid collecting area through the sample loading well outlet.

2. The sample preparation module of claim 1, further comprising a formalin-fixed paraffin-embedded (FFPE) capture insert removable from the sample loading well, wherein the removable cap comprises a plunger.

3. The sample preparation module of claim 1, wherein the elongated body further comprises a purification well.

4. The sample preparation module of claim 3, wherein the purification well contains magnetic microparticles capable of binding to nucleic acid.

5. The sample preparation module of claim 1, wherein the elongated body further comprises one or more reagent compartments.

6. The sample preparation module of claim 1, wherein the elongated body further comprises a pipette tip holder.

7. The sample preparation module of claim 6, wherein the pipette tip holder is preloaded with a pipette tip.

8. An assay cartridge for a PCR-based molecular diagnostic device, said PCR-based molecular diagnostic device comprising an automatic dispense system to transfer the sample using a pipette, said assay cartridge comprising:

- a sample preparation module comprising an elongated body which comprises a sample loading well of an asymmetric shape where a sample is loaded before nucleic acid is extracted from the sample, wherein the sample loading well comprises
  - a generally vertical wall around the sample loading well,
  - a tilted cone shape bottom having a deepest portion,
  - a sample loading well inlet covered by a removable cap, and
  - a sample collecting channel having a sample loading well outlet at its top end and a fluid collecting area at its bottom end,
  - wherein the removable cap has a cap inlet covered by a cap inlet septum having an inlet slit,
  - wherein the sample loading well outlet is covered by a sample loading well outlet septum having an outlet slit,
  - wherein the fluid collecting area is at the deepest portion of the bottom,
  - wherein the pipette is capable of adding the sample to the sample loading well through the sample loading well inlet, and
  - wherein the pipette is capable of collecting the nucleic acid from the fluid collecting area through the sample loading well outlet; and
- a PCR module,
- wherein the sample preparation module and the PCR module is detachably coupled.

9. The assay cartridge of claim 8, wherein the sample preparation module and the PCR module is detachably coupled through a snap.

10. The assay cartridge of claim 8, further comprising a marking element.

11. The assay cartridge of claim 10, wherein the marking element is selected from the group consisting of a barcode, a dot code, a radio frequency identification tag (RFID) and a direct reading electronic memory.

12. The assay cartridge of claim 8, wherein the PCR module comprises

- a push well capable of being loaded with the nucleic acid extracted in the sample preparation module,
- at least one reaction well, and a microfluidic channel connecting a first opening at the bottom of the push well and a second opening at the top of the reaction well.

* * * * *